United States Patent
Yasushi et al.

(10) Patent No.: US 6,870,478 B2
(45) Date of Patent: Mar. 22, 2005

(54) INFORMATION PROVIDING SYSTEM AND INFORMATION PROVIDING METHOD

(75) Inventors: Mitsuo Yasushi, Tsurugashima (JP); Masatoshi Yanagidaira, Tsurugashima (JP)

(73) Assignee: Pioneer Corporation, Tokyo (JP)

( * ) Notice: Subject to any disclaimer, the term of this patent is extended or adjusted under 35 U.S.C. 154(b) by 0 days.

(21) Appl. No.: 10/214,661

(22) Filed: Aug. 7, 2002

(65) Prior Publication Data

US 2003/0043045 A1 Mar. 6, 2003

(30) Foreign Application Priority Data

Aug. 28, 2001 (JP) ..................................... P2001-257434

(51) Int. Cl.⁷ ............................................. G08B 23/00
(52) U.S. Cl. .................... 340/573.7; 340/439; 340/576; 340/5.52; 701/59; 701/209
(58) Field of Search .......................... 340/425.5, 573.1, 340/539.12, 945, 438, 439, 995.19, 995.21, 573.7, 576, 575, 988, 995.1, 995.16, 933, 5.52, 5.82; 701/57, 58, 59, 1, 209, 211; 600/300, 301; 128/903; 180/271, 272

(56) References Cited

U.S. PATENT DOCUMENTS 5,574,641 A    11/1996  Kawakami et al. .... 364/424.05
6,157,317 A  * 12/2000  Walker ................... 340/825.44
6,351,698 B1 *  2/2002  Kubota et al. ................. 701/51
6,459,365 B2 * 10/2002  Tamura .................... 340/425.5
6,542,081 B2 *  4/2003  Torch .......................... 340/575

FOREIGN PATENT DOCUMENTS

| | | |
|---|---|---|
| DE | 100 01 261 A1 | 7/2001 |
| JP | 08-140949 | 6/1996 |
| JP | 10-082653 | 3/1998 |
| JP | 10-253379 | 9/1998 |
| JP | 11-195198 | 7/1999 |
| WO | 98/29847 | 7/1998 |

OTHER PUBLICATIONS

Abstract of JP 08–140949, *Patent Abstracts of Japan*, 2000.

* cited by examiner

*Primary Examiner*—Davetta W. Goins
(74) *Attorney, Agent, or Firm*—Ladas & Parry LLP

(57) ABSTRACT

An information providing system which provides desired information to a driver who drives a vehicle, is provided with: a biomedical information acquisition device which acquires biomedical information of the driver; an on-road driving strain calculating device which calculates on-road driving strain by analyzing road information of a particular segment in a traveling direction of the vehicle; and a driver condition predicting device which predicts physiological condition of the driver in the particular segment by using the acquired biomedical information and the calculated on-road driving strain.

28 Claims, 15 Drawing Sheets

FIG. 2

|  | PHYSIOLOGICAL CONDITION | | |
|---|---|---|---|
|  | TENSION AND IRRITATION | CONCENTRATION | SLEEPINESS AND FATIGUE |
| HEART RATE OF DRIVER A | 70 AND ABOVE | 69~61 | 60~50 |
| HEART RATE OF DRIVER B | 80 AND ABOVE | 79~66 | 65~50 |
| HEART RATE OF DRIVER C | 100 AND ABOVE | 99~81 | 80~50 |
| ... | ... | ... | ... |

INFORMATION PROVIDING SYSTEM AND INFORMATION PROVIDING METHOD

BACKGROUND OF THE INVENTION

1. Field of the Invention

The present invention relates to an information providing system which detects physiological condition of a driver who is driving a vehicle and gives any necessary warning to the driver.

2. Description of the Related Art

Recently, systems have been developed which detect physiological conditions of a vehicle driver such as sleepiness, fatigue, and fretfulness (irritation) during driving and alert the driver to these conditions, thereby encouraging him/her to drive safely.

For example, a system disclosed in Japanese Patent Laid-Open No. 8-140949 detects physiological conditions of a driver such as sleepiness, fatigue, and fretfulness and alerts the driver to any such condition, based on biomedical information such as heartbeat, respiration, fluctuations in heartbeat, and nictitation detected in the driver and road travel data of the vehicle obtained from a navigation system. This makes it possible to detect physiological conditions such as sleepiness, fatigue, fretfulness, etc. of the driver and give warnings even when the vehicle is running.

Such a conventional system issues a warning when the driver is sleepy, tired, fretting, etc. However, when the driver is experiencing, for example, sleepiness, the driver is already in a dangerous situation and even if a warning is issued in such a dangerous case, it is often too late to avoid danger by taking appropriate measures quickly.

Also, the driver can realize, for example, his/her sleepiness all right, but due to errors, the time when the sleepiness is detected by the conventional system does not necessarily coincide with the time when it is realized by the driver. This may bother the driver.

Also, there are great individual variations in biomedical information such as heartbeat, respiration, fluctuations in heartbeat, and nictitation. Thus, conventional systems, which do not take individual variations into consideration, may make an erroneous judgment if the driver changes.

Furthermore, for example, if the driver still has a long way to drive when sleepiness is detected, he/she must be warned, but if the driver arrives soon, he/she need not be warned. However, conventional systems do not give consideration to arrival time.

SUMMARY OF THE INVENTION

It is therefore an object of the present invention to provide an information providing system and an information providing method which make a driver aware of his/her physiological conditions on the road ahead accurately and effectively and thereby avoid danger reliably.

The above object of the present invention can be achieved by an information providing system which provides desired information to a driver who drives a vehicle provided with: a biomedical information acquisition device which acquires biomedical information of the driver; an on-road driving strain calculating device which calculates on-road driving strain by analyzing road information of a particular segment in a traveling direction of the vehicle; and a driver condition predicting device which predicts physiological condition of the driver in the particular segment by using the acquired biomedical information and the calculated on-road driving strain.

According to the present invention, the biomedical information acquisition device acquires biomedical information of the driver and the on-road driving strain calculating device calculates on-road driving strain by analyzing road information of a particular segment in the traveling direction of the vehicle. The biomedical information acquisition device here includes, for example, an MT (minor tremor) pickup, microwave sensor, GSR (galvanic skin response) sensor, etc. Also, the road information includes various information about roads such as information about traffic signals, curves, corners, legal speeds, and traffic. The on-road driving strain means the amount of work strain placed on the driver who is driving on the road. By using the acquired biomedical information and the calculated on-road driving strain, physiological conditions of the driver in a particular segment in the traveling direction of the vehicle are predicted. In this way, the physiological conditions of the driver on the road ahead can be predicted more precisely by using the biomedical information of the driver and the on-road driving strain of the road. Thus, danger can be avoided reliably by making the predicted physiological conditions known to the driver.

In one aspect of the information providing system of the present invention, the driver condition predicting device further judges whether to provide the desired information to the driver based on the predicted physiological condition of the driver.

According this aspect, desired information (e.g., a warning) can be provided to the driver only when it is really necessary based on the predicted physiological conditions of the driver.

In another aspect of the information providing system of the present invention, before or just after the vehicle starts, the driver condition predicting device predicts the physiological condition of the driver in the particular segment by using the acquired biomedical information at the present time and the calculated on-road driving strain with respect to the road to be traveled.

In further aspect of the information providing system of the present invention, when the vehicle is running, the driver condition predicting device predicts the physiological condition of the driver in the particular segment by using the acquired biomedical information at a particular time point during a period from a start of driving to the present time, the acquired biomedical information at the present time, and calculated on-road driving strain with respect to the road to be traveled.

According to this aspect, since the physiological conditions of the driver is predicted by using the biomedical information at a particular time point out of the biomedical information acquired by the biomedical information acquisition device during the period from the start of driving to the present time, the physiological conditions of the driver can be predicted more precisely.

In further aspect of the information providing system of the present invention, the driver condition predicting device predicts the physiological condition of the driver in the particular segment further by using the driver's unique information stored in a database.

According to this aspect, since the physiological conditions of the driver is predicted by using information specific to the driver, the physiological conditions of the driver can be predicted precisely even if there are individual variations, for example, in the relationship between the heart rate and physiological conditions of the driver or between the on-road driving strain and the driver's heart rate.

In further aspect of the information providing system of the present invention, the driver condition predicting device stores a relationship between the acquired biomedical information and the calculated on-road driving strain in a database as the driver's unique information.

According to this aspect, since the driver's unique information can be provided with improved accuracy, the physiological conditions of the driver can be predicted more precisely.

In further aspect of the information providing system of the present invention, the information providing system further is provided with a correction signal input device which inputs a correction signal for correcting deviation between the predicted driver's physiological condition and subjective physiological condition of the driver, wherein when the correction signal is input, the driver condition predicting device corrects the deviation between the predicted physiological condition of the driver and the subjective physiological condition of the driver.

According to this aspect, since any deviation between the predicted physiological conditions of the driver and subjective physiological conditions of the driver can be corrected quickly, the physiological conditions of the driver can be predicted more precisely.

In further aspect of the information providing system of the present invention, when the deviation is corrected, the driver condition predicting device reflects the deviation information in the driver's unique information stored in the database.

According to this aspect, since the driver's unique information can be provided with improved accuracy, the physiological conditions of the driver can be predicted more precisely.

In further aspect of the information providing system of the present invention, the information providing system further is provided with a navigation guidance device which guides the vehicle along its route, wherein the on-road driving strain calculating device selects the particular segment in the traveling direction by using map information obtained from the navigation guidance device.

According to this aspect, a particular segment in the traveling direction of the vehicle can be selected easily by using navigation guidance functions.

In further aspect of the information providing system of the present invention, the on-road driving strain calculating device selects the particular segment in the traveling direction based on the driver's driving history related to the map information.

According to this aspect, a particular segment in the traveling direction of the vehicle can be selected on a route which the driver has traveled in the past.

In further aspect of the information providing system of the present invention, the on-road driving strain calculating device searches for a route to a destination specified by the driver and selects the particular segment in the traveling direction based on the search result.

According to this aspect, a particular segment in the traveling direction of the vehicle can be selected on a route to the destination specified by the driver In further aspect of the information providing system of the present invention, the on-road driving strain calculating device searches for a plurality of routes to the destination specified by the driver, selects the particular segment in the traveling direction in each of the routes, and calculates on-road driving strain by analyzing road information of the particular segment; and the driver condition predicting device predicts the physiological condition of the driver in the particular segment in each of the routes by using the acquired biomedical information and the calculated on-road driving strain and determines a route which will cause less adverse effect on driving from among the plurality of routes based on the result of the prediction.

In further aspect of the information providing system of the present invention, the driver condition predicting device provides to the driver the determined route which will cause less adverse effect on driving.

According to this aspect, danger can be avoided more reliably and a route-finding function in a vehicle navigation system can be made more convenient.

In further aspect of the information providing system of the present invention, the on-road driving strain calculating device calculates on-road driving strain by analyzing the road information in consideration of weather in the particular segment.

According to this aspect, the physiological conditions of the driver can be predicted more precisely.

In further aspect of the information providing system of the present invention, the on-road driving strain calculating device calculates on-road driving strain by analyzing the road information in consideration of time in the particular segment.

According to this aspect, the physiological conditions of the driver can be predicted more precisely.

In further aspect of the information providing system of the present invention, the biomedical information includes heart rate, respiration, fluctuations in heartbeat, nictitation, and complexion.

The above object of the present invention can be achieved by an information providing method which provides desired information to a driver who drives a vehicle provided with: a step of acquiring biomedical information of the driver; a step of calculating on-road driving strain by analyzing road information of a particular segment in a traveling direction of the vehicle; and a driver condition predicting step of predicting physiological condition of the driver in the particular segment by using the acquired biomedical information and the calculated on-road driving strain.

According to the present invention, the physiological conditions of the driver on the road ahead can be predicted more precisely by using the biomedical information of the driver and the on-road driving strain of the road. Thus, danger can be avoided reliably by making the predicted physiological conditions known to the driver.

In one aspect of the information providing method of the present invention, the driver condition predicting step further includes judging whether to provide the desired information to the driver based on the predicted physiological condition of the driver.

The above object of the present invention can be achieved by an information providing method which provides desired information to a driver who drives a vehicle, provided with the steps of: acquiring biomedical information of the driver; searching for a plurality of routes to a destination specified by the driver and calculating on-road driving strain in each of the routes by analyzing road information of a particular segment in a traveling direction of the vehicle; and predicting physiological condition of the driver in the particular segment in each of the routes by using the acquired biomedical information and the calculated on-road driving strain and determining a route which will cause less adverse effect on driving from among the plurality of routes based on the result of the prediction.

According to the present invention, danger can be avoided more reliably and a route-finding function in a vehicle navigation can be made more convenient.

The above object of the present invention can be achieved by an information recorded medium wherein an information providing program for providing desired information to a driver who drives a vehicle, is recorded so as to be read by a computer, the program making the computer function as: a biomedical information acquisition device which acquires biomedical information of the driver; an on-road driving strain calculating device which calculates on-road driving strain by analyzing road information of a particular segment in a traveling direction of the vehicle; and a driver condition predicting device which predicts physiological condition of the driver in the particular segment by using the acquired biomedical information and the calculated on-road driving strain. The driver condition predicting device may judge whether to provide the desired information to the driver based on the predicted physiological condition of the driver. The driver condition predicting device may predict the physiological condition of the driver in the particular segment further by using the driver's unique information stored in a database. When a correction signal for correcting the deviation between the driver's physiological conditions predicted by the driver condition predicting device and subjective physiological conditions of the driver is input, the driver condition predicting device may correct the deviation between the predicted physiological condition of the driver and the subjective physiological condition of the driver.

The present invention can have the same effect as the information providing system when the information providing program is installed in a computer.

The above object of the present invention can be achieved by an information recorded medium wherein an information providing program for providing desired information to a driver who drives a vehicle, is recorded so as to be read by a computer, the program making the computer function as: a biomedical information acquisition device which acquires biomedical information of the driver; an on-road driving strain calculating device which searches for a plurality of routes to a destination specified by the driver and calculates on-road driving strain in each of the routes by analyzing road information of a particular segment in a traveling direction of the vehicle; and a driver condition predicting device which predicts the physiological conditions of the driver in the particular segment in each of the routes by using the acquired biomedical information and the calculated on-road driving strain and determines a route which will cause less adverse effect on driving from among the plurality of routes based on the results of the prediction.

The present invention can have the same effect as the information providing system when the information providing program is installed in a computer.

The above object of the present invention can be achieved by an information providing system which has a server apparatus installed at a fixed location and a terminal apparatus mounted on a vehicle and capable of communicating with the server apparatus via a mobile communications network and which provides desired information to a driver who drives the vehicle, wherein the terminal apparatus is provided with: a biomedical information acquisition device which acquires biomedical information of the driver; and a transmitting device which transmits the acquired biomedical information to the server apparatus via the mobile communications network, and the server apparatus is provided with: a receiving device which receives the biomedical information transmitted from the terminal apparatus; an on-road driving strain calculating device which calculates on-road driving strain by analyzing road information of a particular segment in the traveling direction of the vehicle; and a driver condition predicting device which predicts physiological condition of the driver in the particular segment by using the received biomedical information and the calculated on-road driving strain.

The above object of the present invention can be achieved by a server apparatus provided with: a receiving device which receives biomedical information of a driver transmitted from a terminal apparatus mounted on a vehicle via a mobile communications network; an on-road driving strain calculating device which calculates on-road driving strain by analyzing road information of a particular segment in a traveling direction of the vehicle; and a driver condition predicting device which predicts physiological condition of the driver in the particular segment by using the received biomedical information and the calculated on-road driving strain.

The above object of the present invention can be achieved by a terminal apparatus mounted on a vehicle provided with: a biomedical information acquisition device which acquires biomedical information of a driver; a transmitting device which transmits the acquired biomedical information to a server apparatus via a mobile communications network; a receiving device which receives information about predicted physiological condition of the driver transmitted from the server apparatus via the mobile communications network; and an information providing device which provides the desired information to the driver based on the received information about the physiological condition.

BRIEF DESCRIPTION OF THE DRAWINGS

FIG. 2 is a diagram showing a relationship between heart rates (biomedical information) and physiological conditions of drivers as an example of driver's unique information stored in a database;

FIG. 12 is a flowchart showing details of a deviation correction process in Step S8 of FIG. 7;

DETAILED DESCRIPTION OF THE PREFERRED EMBODIMENTS

Preferred embodiments of the present invention will be described below with reference to the accompanying drawings. The embodiments described below concern cases in which an information providing system according to the present invention is applied to a vehicle navigation system.

(First Embodiment)

Figure 1:
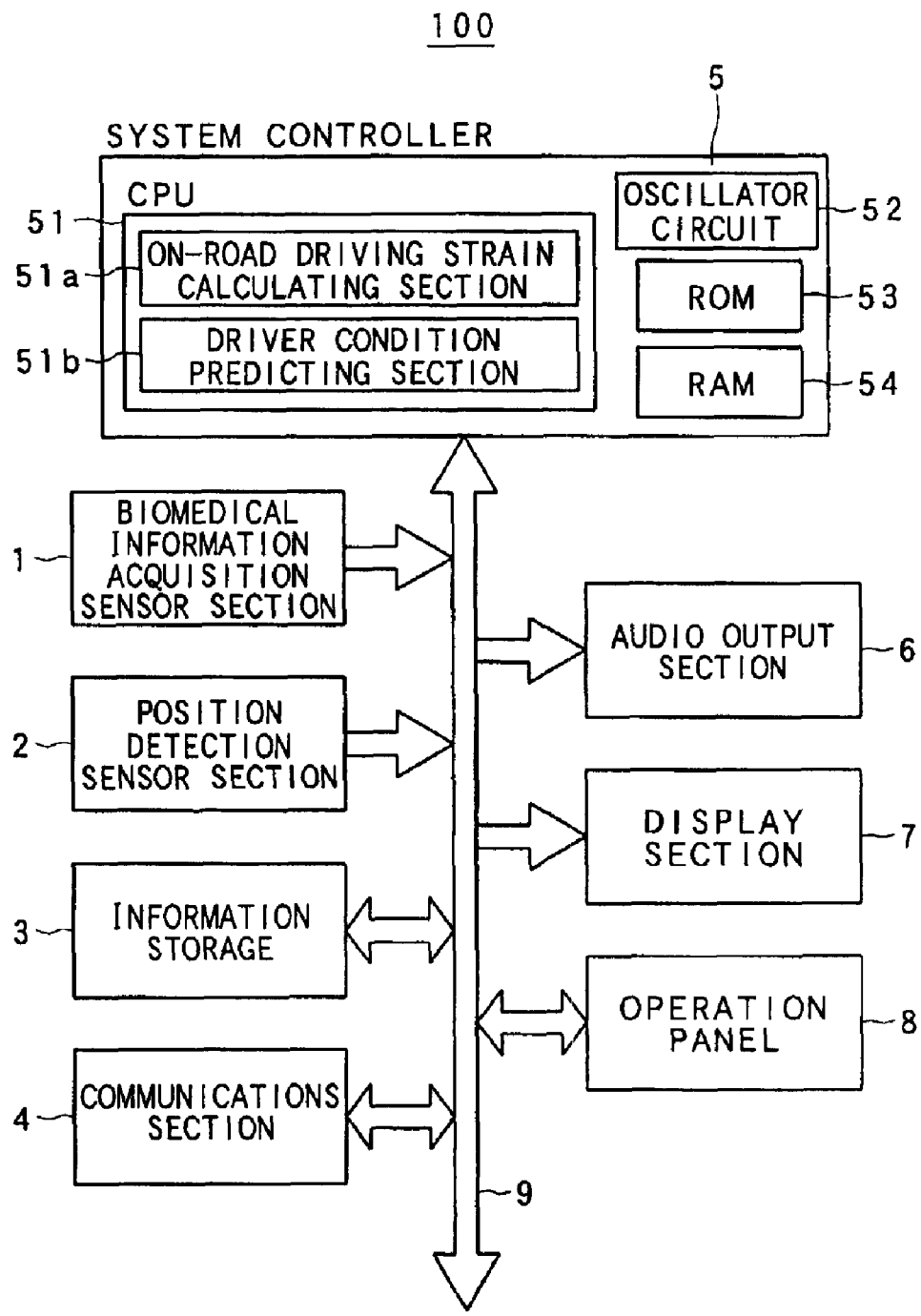
FIG. 1 is a diagram showing a simplified exemplary configuration of a vehicle navigation system according to a first embodiment.

First of all, configuration and functionality of a vehicle navigation system according to a first embodiment will be described with reference to FIGS. 1 to 6. FIG. 1 is a simplified exemplary configuration of the vehicle navigation system according to the first embodiment. As shown in FIG. 1, the vehicle navigation system 100 has navigation guidance functions for guiding a vehicle along its route and includes a biomedical information acquisition sensor section 1, a position detection sensor section 2, an information storage 3, a communications section 4, a system controller 5, an audio output section 6, a display section 7, and a operation panel 8, which are mutually connected via a bus 9.

The biomedical information acquisition sensor section 1 functions as biomedical information acquisition device for acquiring biomedical information of a driver. It includes a known MT pickup, signal processing circuit, etc. This embodiment will be described taking heart rate as an example of biomedical information.

The MT pickup is formed by deposition, for example, on a seat belt at the driver's seat. It detects (picks up) 1- to 10-micron skin tremors which occur on the skin surface of the driver and supplies a skin tremor signal which corresponds to the detected skin tremors to a signal processing circuit.

The signal processing circuit includes an amplifier, BPF (band pass filter), peak hold circuit, LPF (low pass filter), A/D (analog/digital) converter, etc. It generates a heartbeat signal which corresponds to the heartbeat of the driver, based on the skin tremor signal supplied from the MT pickup, and sends it out to the system controller 5 via the bus 9.

Specifically, the skin tremor signal supplied from the MT pickup is amplified by the amplifier. After component shaving frequencies of tens of hertz are extracted by the BPF, the signal is supplied to the peak hold circuit. Peak values at various levels of the skin tremor signal are held by the peak hold circuit and a resulting envelope waveform is supplied as a heartbeat signal to the LPF. After high frequency noise components are removed by the LPF, the heartbeat signal is sampled at designated sampling times by the A/D converter and sent out as a digital heartbeat signal to the system controller 5 via the bus 9.

The position detection sensor section 2 includes various sensors, such as a vehicle speed sensor, acceleration sensor, and GPS (global positioning system) sensor, needed to detect the position of the vehicle as well as interfaces, etc. The vehicle speed sensor detects the mileage and speed of the vehicle based on so-called vehicle speed pulses. The acceleration sensor detects information about the traveling direction of the vehicle by detecting the turning angle and vertical inclination of the vehicle. The GPS sensor receives radio waves broadcast by a GPS satellite by means of a receiver and detects positional information (latitude and longitude) contained in them. The interfaces connect between the sensors and system controller 5 and send out the information detected by the sensors to the system controller 5 via the bus 9.

The information storage 3 includes a read-only storage unit such as a CD (compact disc)-ROM drive or DVD (digital versatile disc)-ROM drive; and a readable/writable storage unit such as a hard disk drive, CD-R/W drive, or DVD-RAM drive. A read-only recording medium (such as CD-ROM or DVD-ROM) which is detachably mounted in the read-only storage unit stores map information including road information (road types, road shapes, legal speeds for roads) necessary for navigation guidance and calculation of on-road driving strain described later. The read-only storage unit reads necessary information from the read-only recording medium at the instruction of the system controller 5 and sends it out to the system controller 5 or the like via the bus 9.

The readable/writable recording medium (hard disk, CD-R/W, or DVD-RAM) mounted in the readable/writable storage unit stores the map information transferred from the read-only recording medium. Also, it stores drivers' driving history related to the map information for each driver separately. Furthermore, a database has been constructed logically in the readable/writable recording medium to store driver's unique information. The database stores driver's unique information for each driver separately.

FIG. 2 shows a relationship between heart rates (biomedical information) and physiological conditions of drivers, based on actual measured data, as an example of the driver's unique information stored in the database. As shown in the figure, all drivers A, B, and C tend to have a high heart rate when tense or irritated, and a low heart rate when sleepy or tired. However, the relationship between the heart rate and physiological conditions varies from driver to driver: there are individual variations. For example, whereas driver A has a heart rate of 69 to 61 when he is driving in concentration, driver B has a heart rate of 79 to 66 when he is driving in concentration.

Besides, the database stores a relationship between on-road driving strain and heart rate of each driver. The relationship between on-road driving strain and a driver's heart rate shows how the heart rate changes with on-road driving strain.

Incidentally, before driver's unique information is stored, the database contains typical relationship between heart rates and physiological conditions of drivers, typical relationship between on-road driving strain and drivers' heart rates, etc.

The communications section 4 has known capabilities of running predetermined input interface processes on signals transmitted from a center station (not shown; or an information server connected to the center station) via a mobile communications network and outputting the signals to the system controller 5 as well as running predetermined output interface processes on any incoming signal to be transmitted from the system controller 5 to the center station (not shown) and outputting the signal to a server 22 via the mobile communications network 23. The communications section 4 is used mainly to obtain road traffic information and weather information. The traffic information and weather information may be obtained from information and communication facilities installed along roads using a known VICS (vehicle information communication system). The system controller 5 is provided with a CPU 51 which performs computational functions as a computer of the present invention, an oscillator circuit 52, a ROM 53 which stores programs and data, including information providing programs of the present invention, for controlling various operations, a RAM 54 which serves as a working area. It controls the operation of the entire vehicle navigation system 100 and has clock functions. The information providing programs stored in the ROM 53 make the CPU 51 function as an on-road driving strain calculating section 51a and a driver condition predicting section 51b, which correspond, respectively, to the on-road driving strain calculating device and driver condition predicting device. Functions of the on-road driving strain calculating section 51a and driver condition predicting section 51b will be described in detail below.

The on-road driving strain calculating section 51a has a function to calculate on-road driving strain by analyzing the road information of a particular segment in the traveling direction of the vehicle. The particular segment in the traveling direction of the vehicle is selected by using map information obtained from navigation guidance functions which guide a vehicle along a route. For example, the on-road driving strain calculating section 51a searches for a route (the most suitable route) to the destination specified by the driver and selects a particular segment in the traveling direction based on search results.

Also, the on-road driving strain calculating section 51a can select a particular segment in the traveling direction based on the driver's driving history related to the map information. Furthermore, even if no driving history of the driver is available, the on-road driving strain calculating section 51a can estimate the driving route of the vehicle based on the current location and traveling direction and select a segment on the route as the particular segment in the traveling direction.

According to this embodiment, the on-road driving strain calculating section 51a divides the selected segment further into a plurality of segments (hereinafter referred to as sub-segments) and calculates on-road driving strain by analyzing road information every such sub-segment. A sub-segment may be set to any length. On-road driving strain Wroad is calculated, for example, with Equation (1) below.

$$W\text{road} = Ws * Wc * Ww * Wt \qquad (1)$$

where Ws is the driving strain due to vehicle speed, Wc is the driving strain due to driving operations, Ww is the driving strain due to weather, and Wt is the driving strain due to time of day (hours). Each of them is represented by a numeric value between 0 and 1.

More specifically, Ws is an amount which represents the effect of vehicle speed on driver strain. It increases in proportion to the increase in vehicle speed. For example, if a reference vehicle speed is taken as 40 km/h at which Ws=0.5, then Ws=0.6 at a vehicle speed of 60 km/h and Ws=0.4 at a vehicle speed of 20 km/h. In this way, Ws is considered to increase in proportion to the increase in vehicle speed because the higher the vehicle speed, the narrower the field of vision will become and the more attention the driver must pay to the surrounding circumstances. The vehicle speed in each sub-segment is estimated, for example, from legal speed contained in the road information. Also, Ws is determined, taking into consideration traffic information (congestion information). For example, the on-road driving strain calculating section 51a acquires from the traffic information whether each sub-segment is currently congested, assesses whether it will be congested at the time of passage, and if it will be, the on-road driving strain calculating section 51a reduces the value of Ws by a certain proportion.

Wc is an amount which represents the effect of driving operations such as steering operations, brake operations, accelerator operations, and clutch operations on driver strain. It increases in proportion to the increase in the number of driving operations. For example, if a reference number of driving operations is taken as 10 at which Wc=0.5, then Wc=0.6 when the number of driving operations is 15 and Wc=0.4 when the number of driving operations is 5. The number of driving operations in each sub-segment is estimated from each number of traffic signals, curves, and corners contained in traffic information. For example, if there are three curves and two corners in a sub-segment, it is assumed that there will be three brake operations at the curves and two steering operations and two brake operations at the corners, and thus the number of driving operations in this sub-segment will be seven (3 brake operations+2 steering operations+2 brake operations=7).

Ww is an amount which represents the effect of weather on driver strain. It changes with weather conditions. For example, Ww=0.1 when it is fine, Ww=0.3 when it rains lightly, Ww=0.7 when it rains heavily, and Ww=0.9 when it snows. The weather in each sub-segment is the weather during upcoming passage through that sub-segment. It is estimated based on current weather in that sub-segment obtained from weather information.

Wt is an amount which represents the effect of the time of day (hours) on driver strain. It changes with the time of day (hours). For example, from around 7 a.m. to around 9 a.m., the driving strain is set at a small value of Wt=0.1, considering that generally the driver is feeling refreshed; from around 1 p.m. to around 3 p.m., the driving strain is set at a large value of Wt=0.7, considering that generally the driver is feeling sleepy; from around 7 p.m. to around 11 p.m., the driving strain is set at a rather large value of Wt=0.5, considering general darkness, poor visibility, etc.; at 11 p.m. and later, the driving strain is set at a very large value of Wt=0.9, considering that generally the driver is feeling very sleepy. The time of day (hours) is the time of upcoming passage through that sub-segment. It is estimated based on the present time, vehicle speed, road conditions, etc.

The driver condition predicting section 51b has a function to predict physiological conditions of the driver in the particular segment using the biomedical information (heart rate, in this case) acquired by the biomedical information acquisition sensor section 1 and the on-road driving strain Wroad calculated by the on-road driving strain calculating section 51a.

Figure 3A:
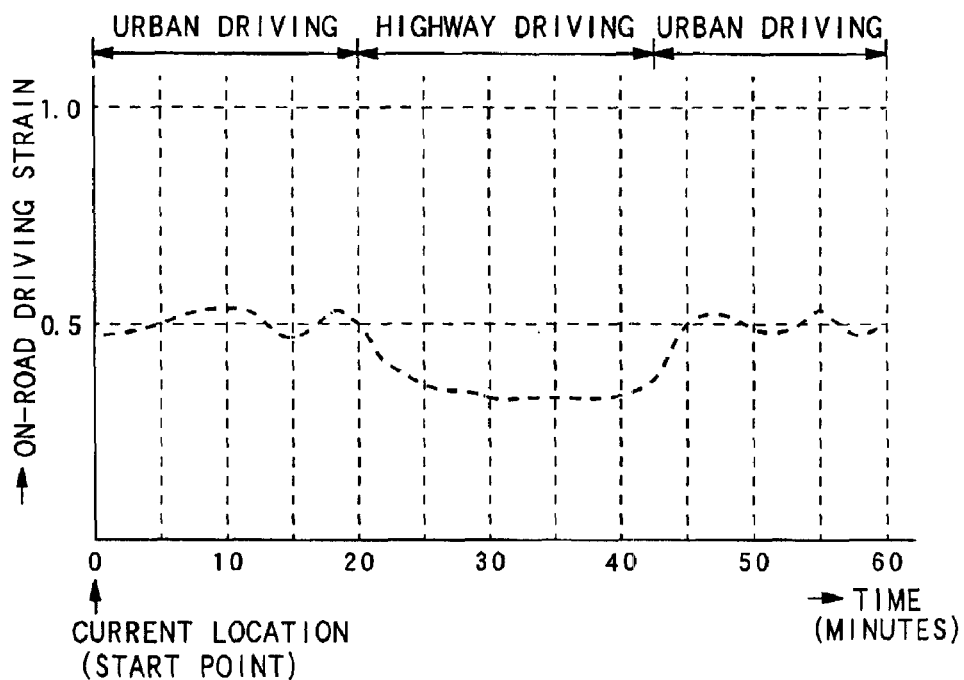
FIG. 3A is a diagram showing an example of changes in on-road driving strain Wroad expressed as a function of time.

More specifically, the driver condition predicting section 51b converts the on-road driving strain Wroad calculated for consecutive sub-segments in the particular segment into a function of time. FIG. 3A shows an example of changes in on-road driving strain Wroad expressed as a function of time. In the example of FIG. 3A, from the current time to about 20 minutes of driving, when the vehicle runs on an urban road, the on-road driving strain Wroad is large and fluctuates, whereas between about 20 and 40 minutes of driving, when the vehicle runs on a highway, the on-road driving strain Wroad is small and nearly constant.

The driver condition predicting section 51b converts the changes in on-road driving strain Wroad thus obtained into changes in heart rate according to certain rules, taking into consideration the heart rate acquired by the biomedical information acquisition sensor section 1. The certain rules here mean rules found by experience and include, for example, rules that: (a) during a period in which on-road driving strain Wroad fluctuates within a certain range, the heart rate does not fluctuate much, (b) during a period in which on-road driving strain Wroad is constant, the heart rate decreases at a certain rate, and (c) during a period in which on-road driving strain Wroad increases sharply, the heart rate increases at a certain rate.

Figure 3B:
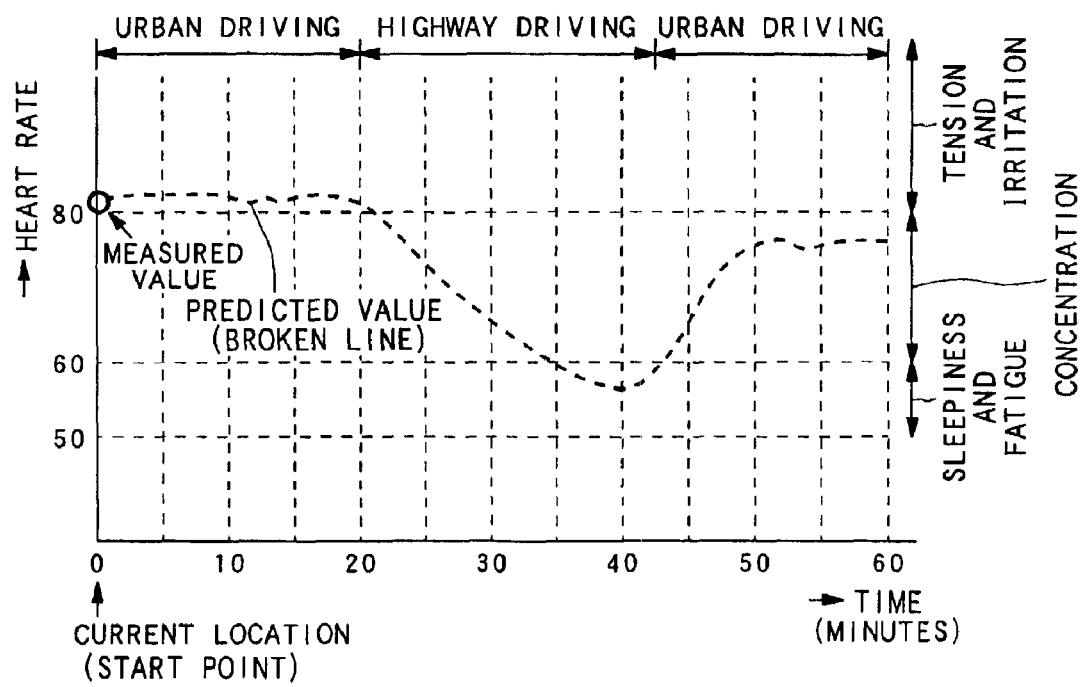
FIG. 3B is a diagram showing an example of changes in heart rate predicted by a driver condition predicting section 51b.

FIG. 3B shows an example of changes in heart rate predicted by the driver condition predicting section 51b. As shown in the drawing, beginning with the heart rate (measured value) acquired by the biomedical information acquisition sensor section 1, the heart rate (predicted value) is nearly constant from the current time to about 20 minutes of driving when the on-road driving strain Wroad fluctuates. It decreases at a certain rate between about 20 and 40 minutes of driving when the on-road driving strain Wroad is nearly constant. Then, it increases and stabilizes approximately 20 minutes after that period when the on-road driving strain Wroad fluctuates again.

The driver condition predicting section 51b predicts the physiological conditions of the driver based on such changes in the heart rate and the relationship between the driver's heart rate and physiological conditions stored in the database described earlier. In the example of FIG. 3B, the driver condition predicting section 51b predicts that the driver will be sleepy or tired if the heart rate is 50 to 60, that the driver will be driving in concentration if the heart rate is 61 to 80, and that the driver will be tense or irritated if the heart rate is 81 or above. In the example of FIG. 3B, it can be seen that the driver will concentrate after approximately 21 minutes counting from the current location and will get sleepy and tired after approximately 35 minutes counting from the current location.

However, as described earlier, there are individual variations in the relationship between the heart rate and physiological conditions of the driver or between the on-road driving strain and driver's heart rate. Regarding individual variations in the relationship between the heart rate and physiological conditions of the driver, for example, whereas the heart rate of between 61 and 80 corresponds to concentration in the case of FIG. 3B (typical relationship), the heart rate of between 61 and 69 corresponds to concentration in the case of driver A in FIG. 2. Regarding individual variations in the relationship between the on-road driving strain Wroad and the driver's heart rate, for example, the heart rate decreases at nearly a constant rate between about 20 and 40 minutes of driving in the case of FIG. 3B, but the decrease rate varies slightly with the driver.

Therefore, if driver's unique information is stored in the database, the driver condition predicting section 51b predicts the physiological conditions of the driver using the information specific to that driver (relationship between the heart rate and physiological conditions of the driver or between the on-road driving strain Wroad and driver's heart rate). This makes it possible to predict the physiological conditions of the driver more precisely. Incidentally, the identity of a driver is determined, for example, based on instructions from the operation panel 8.

In the example described above with reference to FIGS. 3A and 3B, in which the vehicle is about to start or has just started(before or just after the vehicle starts), the driver condition predicting section 51b predicts the physiological conditions of the driver in the particular segment using the current biomedical information and the on-road driving strain Wroad of the road to be traveled. However, if the vehicle is running, the driver condition predicting section 51b can predict the physiological conditions of the driver more precisely by using the acquired biomedical information at a particular time point(or in a particular segment) during a period from a start of driving to the present time, the acquired biomedical information at the present time, calculated on-road driving strain Wroad of the road traveled from the start of driving to the present time, and on-road driving strain Wroad of the road to be traveled. Incidentally, the on-road driving strain Wroad of the road traveled from the start of driving to the present time many be the on-road driving strain Wroad in the particular road segment traveled from the start of driving to the present time.

Figure 4A:
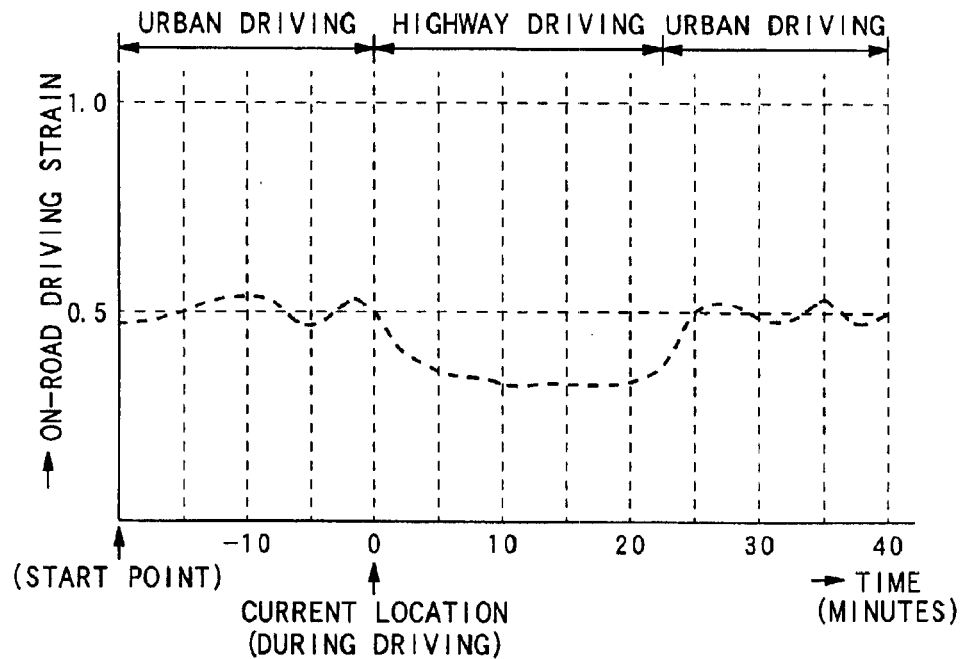
FIG. 4A is a diagram showing an example of changes in on-road driving strain Wroad expressed as a function of time in the case where a vehicle is running.
Figure 4B:
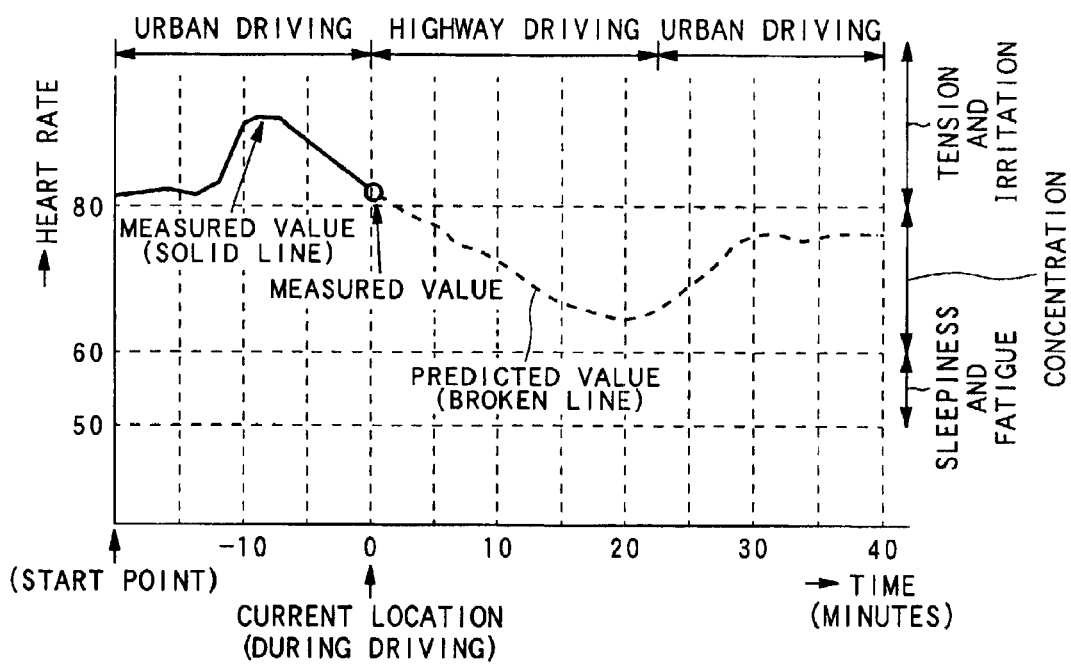
FIG. 4B is a diagram showing an example of changes in heart rate predicted by the driver condition predicting section 51b in the case where the vehicle is running.

FIG. 4A shows an example of changes in on-road driving strain Wroad expressed as a function of time in the case where the vehicle is running. FIG. 4B shows an example of changes in heart rate predicted by the driver condition predicting section 51b in the case where the vehicle is running. The example of FIG. 4A shows changes in on-road driving strain Wroad of the road traveled during the period from the start of driving to the present time as well as changes in on-road driving strain Wroad of the road to be traveled. In the example of FIG. 4B, measured values are used as the heart rate at and before the current location.

When the vehicle is running, the driver condition predicting section 51b converts the changes in on-road driving strain Wroad of the road to be traveled (during the period from the present time to 40 minutes in FIG. 4A) into changes in heart rate (during the period from the present time to 40 minutes in FIG. 4B) according to certain rules, taking into consideration the current heart rate. In addition to the rules ((a) to (c) above) applicable to the vehicle before or just after start, the certain rules mentioned here include rules that: (d) if the heart rate increased sharply in the period from the start of driving to the present time, the heart rate decreases at a smaller rate during the subsequent period in which the on-road driving strain Wroad is constant than in the absence of such a sharp increase, (e) if the heart rate decreased at a constant rate up to the present time, this decrease rate is taken into consideration subsequently, and (f) if on-road driving strain Wroad was large during the period from the start of driving to the present time, the heart rate decreases at a larger rate during the subsequent period in which the on-road driving strain Wroad is constant than in a case where the on-road driving strain Wroad was small. Whether rules (d) and (e) are applicable is judged based on the biomedical information from the start of driving to the present time and whether rule (f) is applicable is judged based on the on-road driving strain Wroad from the start of driving to the present time.

According to the changes in heart rate predicted by the driver condition predicting section 51b in FIG. 4B, the decrease rate in heart rate during the highway driving is smaller than the decrease rate in heart rate during the highway driving in FIG. 3B. Consequently, the physiological conditions of the driver are such that the driver is not sleepy or tired yet. This is because rule (d) above was applied as the heart rate increased sharply at a time point (e.g., when a child jumped out) during travel from the start point to the current location.

Also, the driver condition predicting section 51*b* stores the relationship between the biomedical information and on-road driving strain Wroad of the road from the start of driving to the present time in the database as driver's unique information by associating it with the given driver. This makes it possible to gradually improve the accuracy of the relationship between the biomedical information of the driver and on-road driving strain Wroad stored for each driver in the database.

Incidentally, when the vehicle is running, the driver condition predicting section 51*b* may predict the physiological conditions of the driver by using either biomedical information at a particular time point during a period from a start of driving to the present time or the on-road driving strain Wroad from the start of driving to the present time. Also, the physiological conditions of the driver maybe predicted using neither. Besides, even when the vehicle is running, if driver's unique information is stored in the database, the information specific to that driver can be used in predicting his/her physiological conditions.

As described above, after predicting the physiological conditions of the driver, the driver condition predicting section 51*b* determines whether to provide desired information to the driver. The desired information mentioned here include, for example, a warning (character display or audio output) that the driver will get sleepy in a few tens of minutes.

Figure 5A:
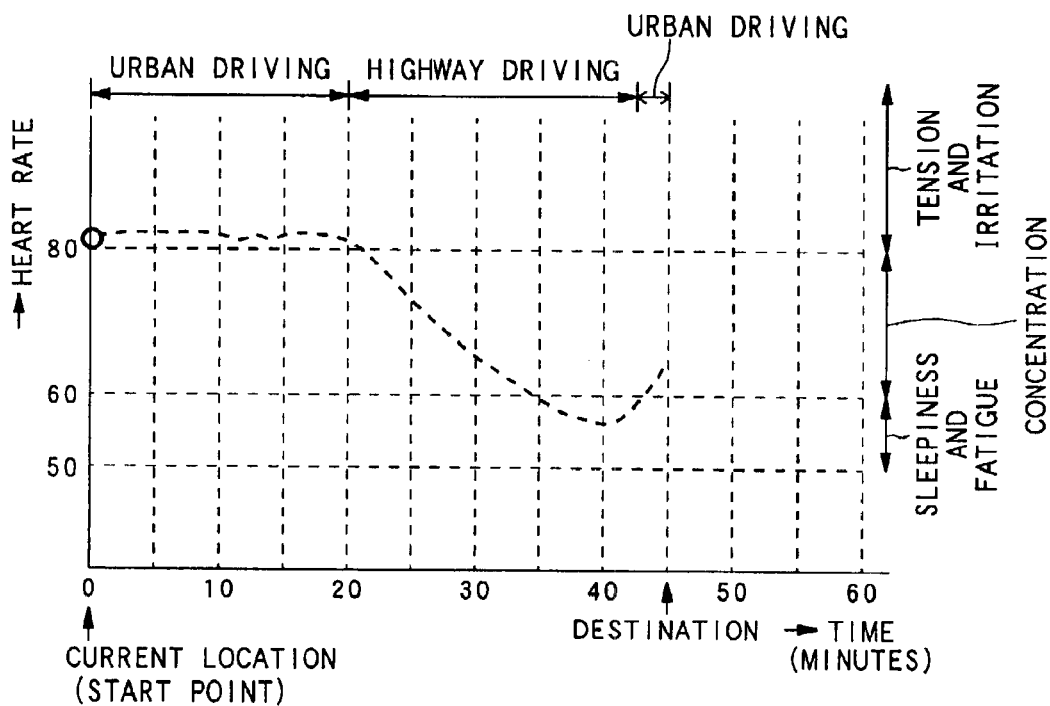
FIG. 5A is a diagram showing an example of changes in heart rate predicted by the driver condition predicting section 51b in the case where a warning is given.
Figure 5B:
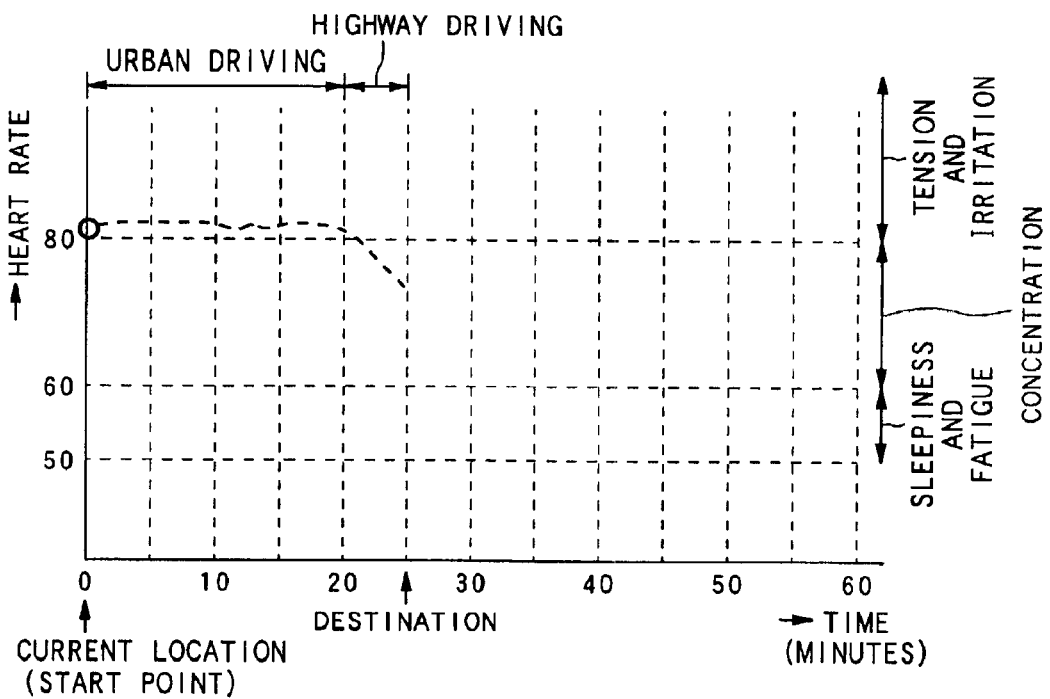
FIG. 5B is a diagram showing an example of changes in heart rate predicted by the driver condition predicting section 51b in the case where a warning is not given.

FIG. 5A shows an example of changes in heart rate predicted by the driver condition predicting section 51*b* in the case where a warning is given. FIG. 5B shows an example of changes in heart rate predicted by the driver condition predicting section 51*b* in the case where a warning is not given.

A destination has been specified by the driver in both FIGS. 5A and 5B, and the destination in FIG. 5A has been set at a more distant place than the destination in FIG. 5B. Consequently, in the case of FIG. 5A, there is a period in which the driver will get sleepy before he arrives at the destination, whereas in the case of FIG. 5B, there is no such period. Thus, in the case of FIG. 5B, the system controller 5 judges it unnecessary to warn the driver and does not give warning to the driver, whereas in the case of FIG. 5A, the system controller 5 judges it necessary to give a warning and warns the driver that he will get sleepy, for example, after 35 minutes.

Returning to FIG. 1, the audio output section 6 includes an audio processing circuit, speaker, etc. The audio processing circuit amplifies audio signals to an appropriate level and outputs them to the speaker according to instructions from the system controller 5. Examples of such audio signals include voices for guiding the vehicle along its route and voices warning the driver in the manner described above.

The display section 7 includes a display control circuit, buffer memory, display screen, etc. The display control circuit generates display data to be displayed on the display screen and temporarily stores it in the buffer memory, and then reads it from the buffer memory and displays it on the display screen in a timely manner, according to instructions from the system controller 5. Examples of such display data include guidance screens for guiding the vehicle along its route and character display for warning the driver in the manner described above.

Figure 6:
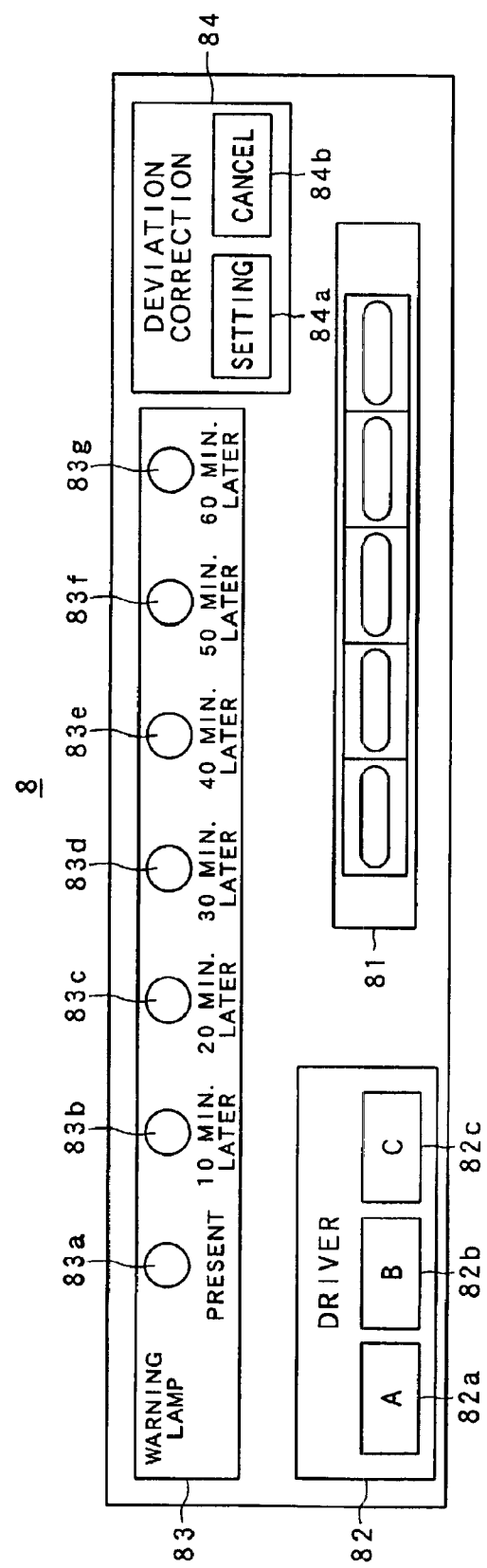
FIG. 6 is a diagram showing an exemplary external configuration of a operation panel 8.

The operation panel 8 has various buttons arranged on it in order for the driver to perform desired operations for vehicle navigation. It is installed, for example, on the body of the vehicle navigation system 100. FIG. 6 shows an exemplary external configuration of the operation panel 8. As shown in the figure, the operation panel 8 is equipped with operation buttons 81, driver selection buttons 82, warning lamps 83, and deviation correction buttons 84. When a button among the operation buttons 81, driver selection buttons 82, or deviation correction buttons 84 is pressed, an appropriate detection signal is sent out to the system controller 5 via the bus 9.

The operation buttons 81 are intended for use by the driver in entering instructions in order to specify a destination or find a route. They include such buttons that are installed in known vehicle navigation systems.

The driver selection buttons 82 are intended for use in setting a driver. They include driver A, B, and C buttons 82*a*, 82*b*, and 82*c*. As a button is pressed, the driver can be identified. For example, if driver A, who is going to drive the vehicle, presses the driver A button 82*a*, the system controller 5 recognizes the press of the button and reads the unique information to driver A from the database to use it for prediction of physiological conditions.

The warning lamps 83 are intended to give warnings to the driver in an easy-to-understand manner based on prediction of driver's physiological conditions. They include lamps 83*a* to 83*g* organized stepwise corresponding to Present, 10 Min. Later, . . . , 60 Min. Later. For example, they glow blue if tension and irritation is predicted, glow yellow if concentration is predicted, and glow red—which is a warning display—if sleepiness and fatigue is predicted. For example, if it is predicted that the driver will get sleepy and tired in 40 minutes, but otherwise will drive in concentration, the lamp 83*e* which corresponds to 40 Minutes Later will glow red and the other lamps will glow yellow. This will show the driver at a glance how many minutes later he will get sleepy.

The deviation correction buttons 84 function as correction signal input device. It is intended for use in giving an instruction to correct a deviation between the physiological conditions of the driver predicted by the driver condition predicting section 51*b* and subjective physiological conditions of the driver. They include a setting button 84*a* and cancel button 84*b*.

For example, when driver A in FIG. 2 is driving the vehicle and his heart rate is 65, if the driver condition predicting section 51*b* predicts driver A's concentration according to FIG. 2 and illuminates the "Present" lamp 83*a* in yellow (concentration) from among the warning lamps 83. However, if driver A himself feels sleepy, this means that there is a discrepancy between the physiological condition of the driver predicted by the driver condition predicting section 51*b* and subjective physiological condition of the driver.

In such a case, if driver A presses the setting button 84*a*, the driver condition predicting section 51*b* corrects the deviation between the predicted physiological condition (concentration) and subjective physiological condition (sleepiness) of the driver. For example, it makes a correction to driver A's heart rate retrieved from the database: it increases the heart rate at which driver A starts to feel sleepy from 60 to 65 so as to increase detection sensitivity to sleepiness. Also, the driver condition predicting section 51*b* reflects the deviation information (e.g., information about the change from 60 to 65 made to the heart rate at which driver A starts to feel sleepy) in the driver A's unique information stored in the database. This makes it possible to predict the physiological conditions of the driver more precisely.

On the other hand, when driver A in FIG. 2 is driving the vehicle and his heart rate is 56, the driver condition predicting section 51b predicts driver A's sleepiness according to FIG. 2 and illuminates the "Present" lamp 83a in red (sleepiness) from among the warning lamps 83. However, if driver A himself is conscious of his concentration, this means that there is a discrepancy between the physiological condition of the driver predicted by the driver condition predicting section 51b and subjective physiological condition of the driver.

In such a case, if driver A presses the cancel button 84b, the driver condition predicting section 51b corrects the deviation between the predicted physiological condition (sleepiness) and subjective physiological condition (concentration)of the driver. For example, it makes a correction to driver A's heart rate retrieved from the database: it decreases the heart rate at which driver A starts to feel sleepy from 60 to 55 so as to decrease detection sensitivity to sleepiness. Also, the driver condition predicting section 51b reflects the deviation information (e.g., information about the change from 60 to 55 made to the heart rate at which driver A starts to feel sleepy) in the driver A's unique information stored in the database.

Figure 7:
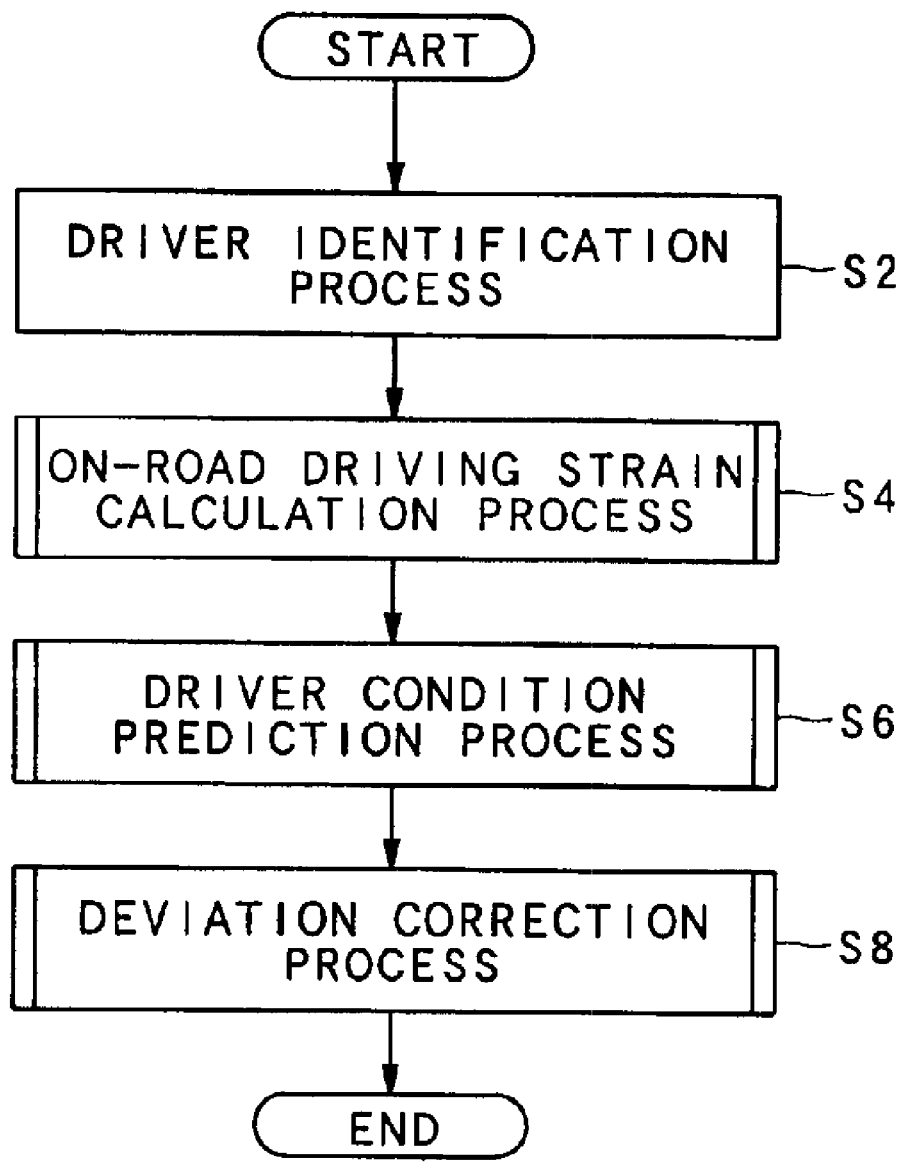
FIG. 7 is a diagram showing a simplified flow which takes place in a CPU 51 of a system controller 5.
Figure 8:
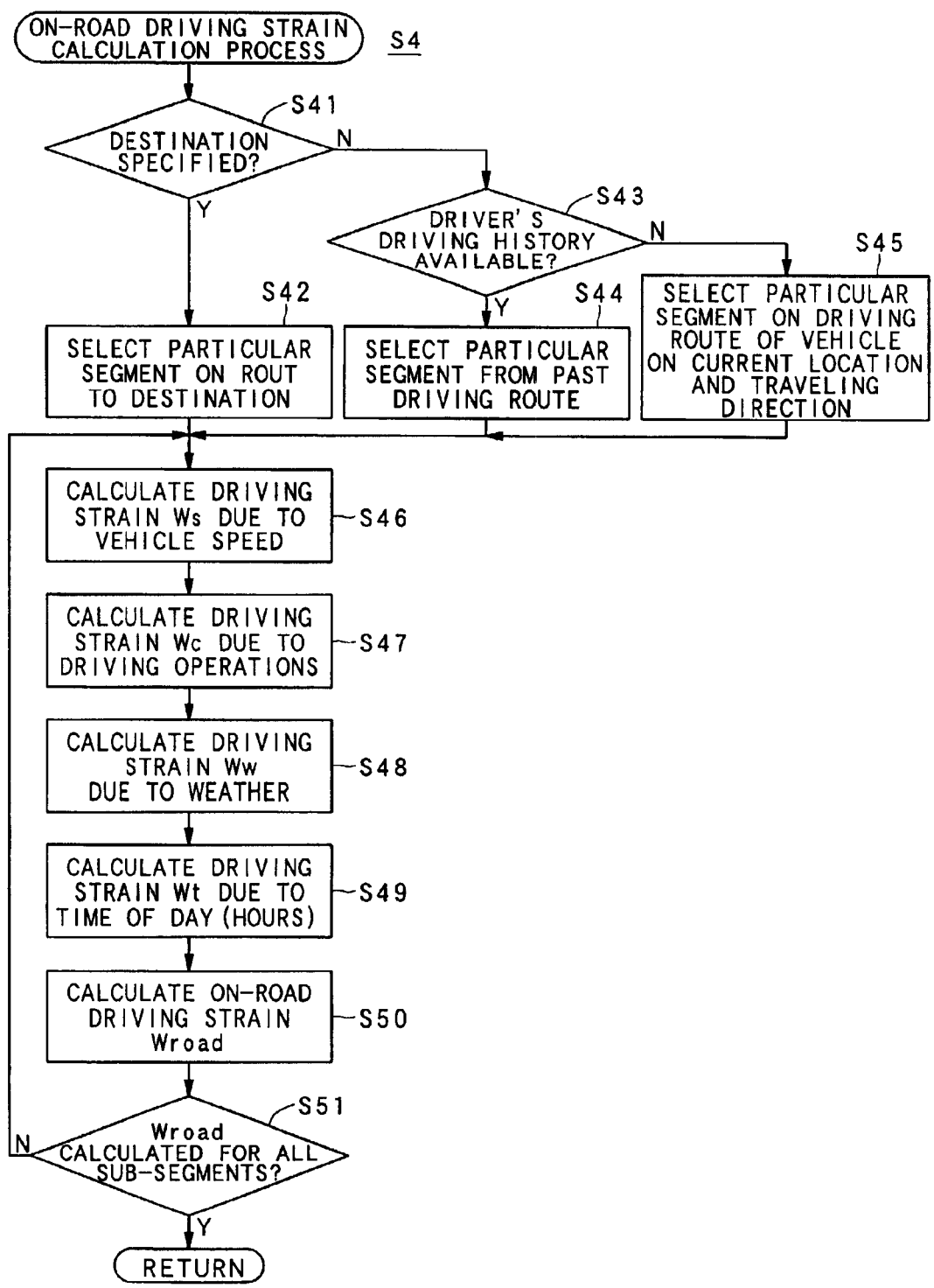
FIG. 8 is a flowchart showing details of an on-road driving strain calculation process in Step S4 of FIG. 7.
Figure 9:
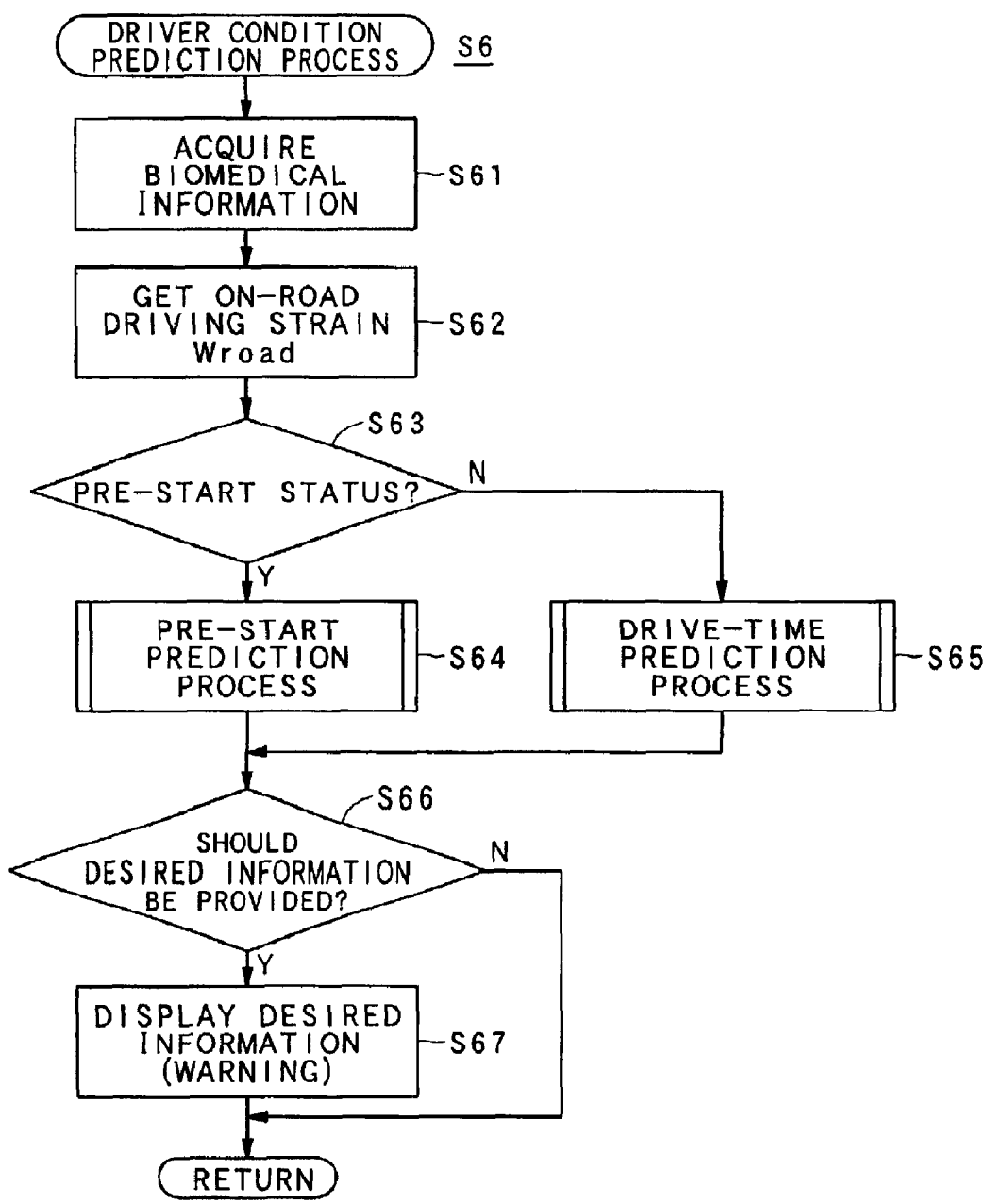
FIG. 9 is a flowchart showing details of a driver condition prediction process in Step S6 of FIG. 7.
Figure 10:
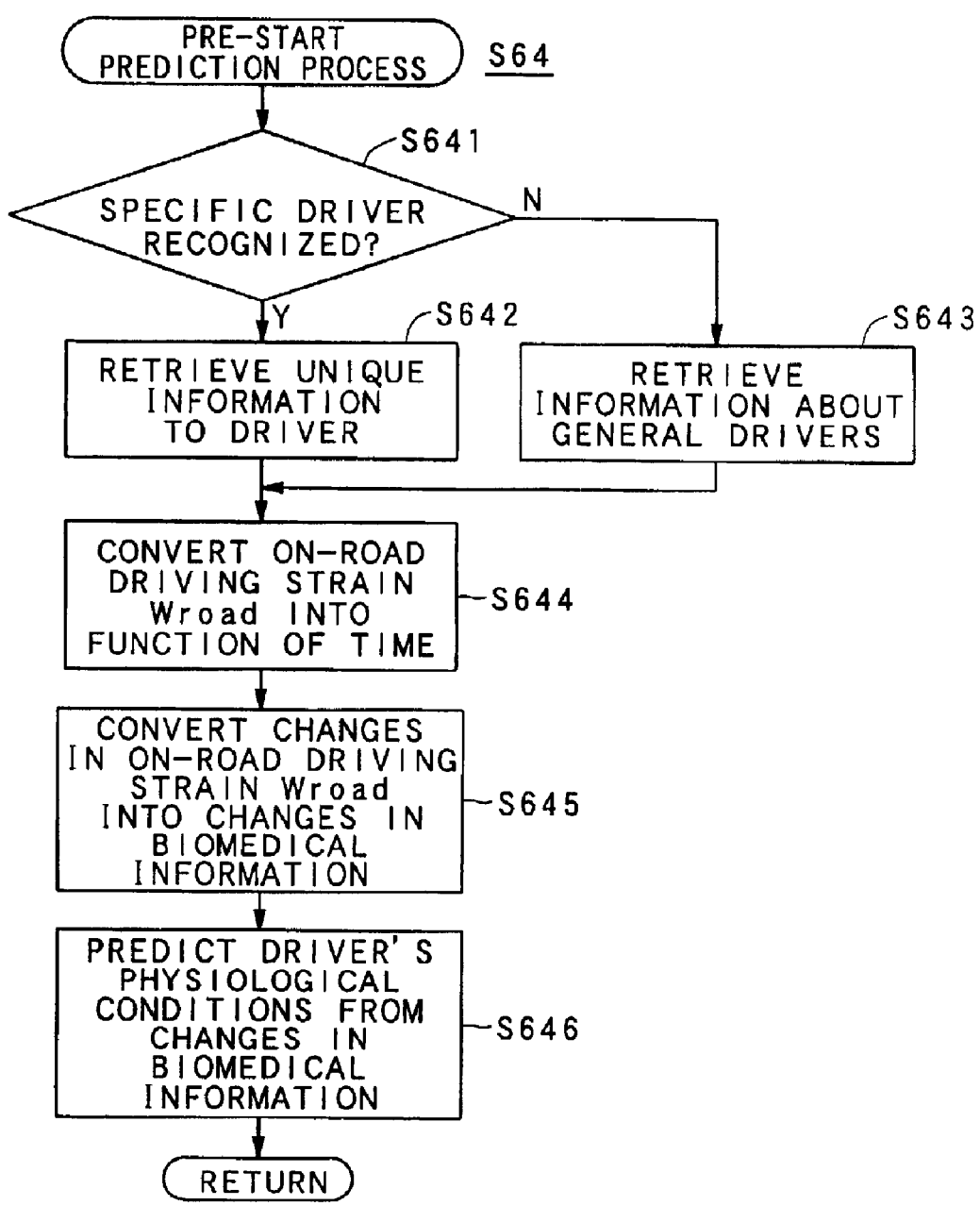
FIG. 10 is a flowchart showing details of a pre-start prediction process in Step S64 of FIG. 9.
Figure 11:
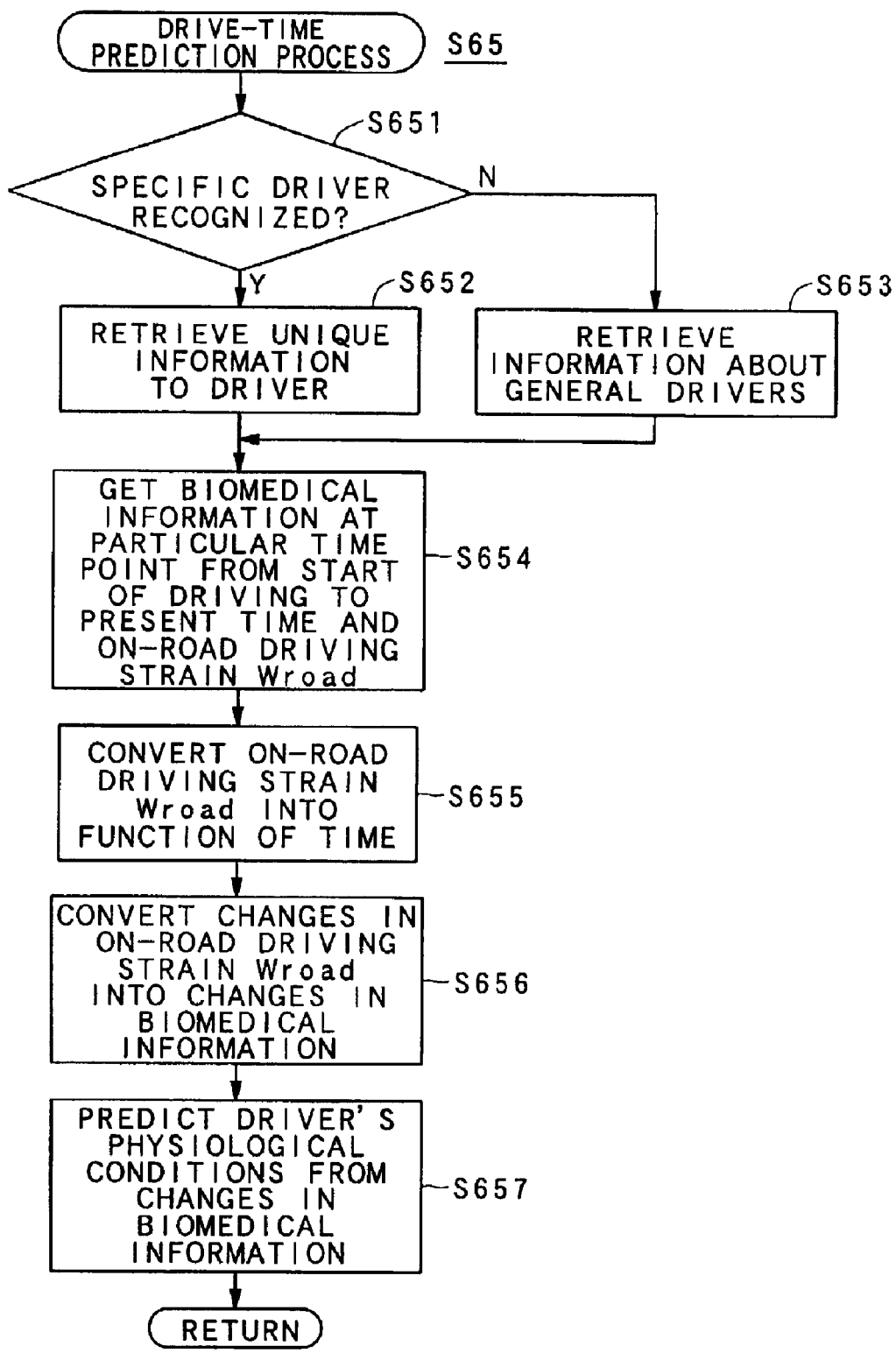
FIG. 11 is a flowchart showing details of a drive-time prediction process shown in Step S65 of FIG. 9.
Figure 1:
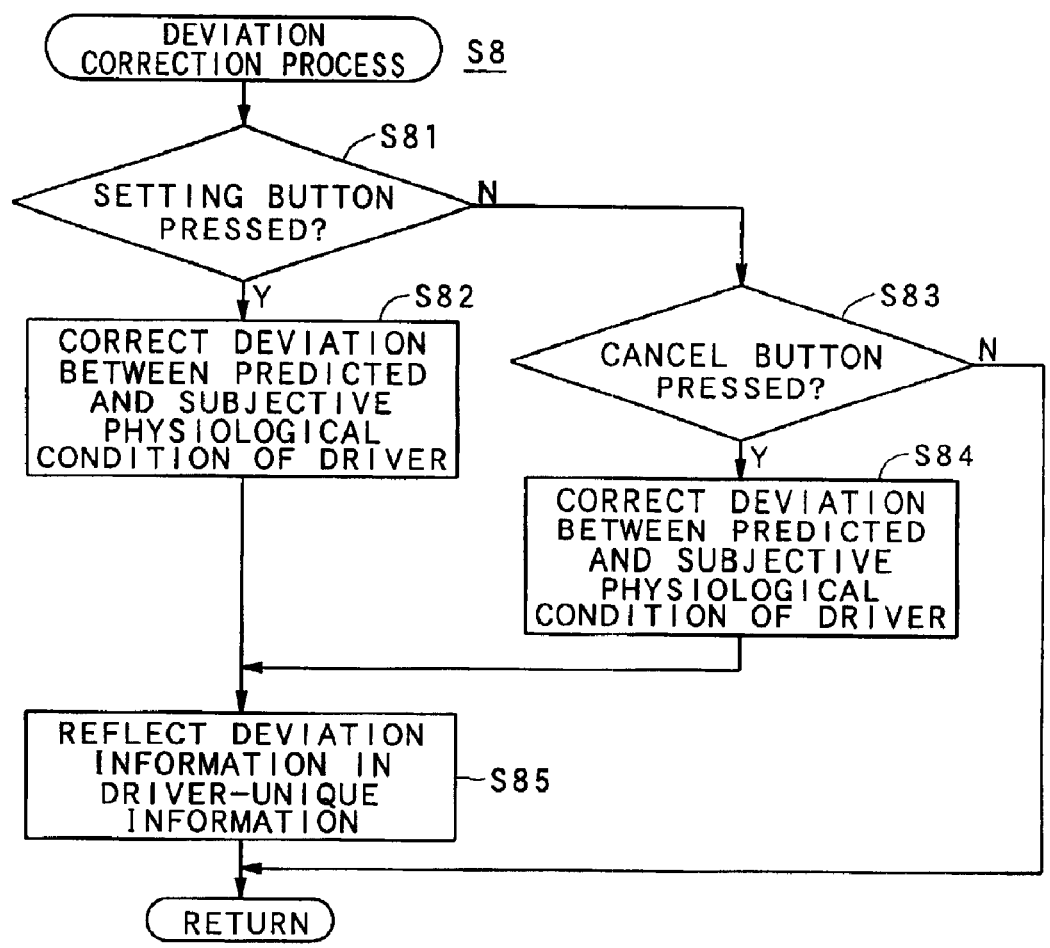

Next, the operation of the vehicle navigation system 100 will be described with reference to FIGS. 7 to 12. FIG. 7 is a diagram showing a simplified flow which takes place in the CPU 51 of the system controller 5. FIG. 8 is a flowchart showing details of an on-road driving strain calculation process in Step S4 of FIG. 7. FIG. 9 is a flowchart showing details of a driver condition prediction process in Step S6 of FIG. 7. FIG. 10 is a flowchart showing details of a pre-start prediction process in Step S64 of FIG. 9. FIG. 11 is a flowchart showing details of a drive-time prediction process shown in Step S65 of FIG. 9. FIG. 12 is a flowchart showing details of a deviation correction process in Step S8 of FIG. 7.

Information processing programs for performing the above processes are stored, for example, in the ROM 53 and are read and executed by the CPU 51 upon engine start or according to instructions from the operation panel 8.

In the driver identification process (Step S2) of FIG. 7, the CPU 51 judges whether a driver is set via the driver selection buttons 82 on the operation panel 8, i.e., whether any of the driver A, B, and C buttons 82a, 82b, and 82c is pressed. If any of these buttons is pressed, the CPU 51 recognizes the driver who corresponds to the pressed button.

Regarding the method for recognizing (identifying) the driver, instead of using the driver selection buttons 82 on the operation panel 8, drivers may be identified by analyzing cardiac waveforms based on the heart rate acquired by the biomedical information acquisition sensor section 1. Drivers may also be identified by their personal identification number on their car keys. Furthermore, drivers may be identified by a car seat or mirror location.

In the on-road driving strain calculation process (Step S4) of FIG. 7, as shown in FIG. 8, the on-road driving strain calculating section 51a of the CPU 51 judges whether a destination has been specified (Step S41). If it is judged that a destination has been specified, the on-road driving strain calculating section 51a obtains map information from the information storage 3, searches for a route to the destination, and selects a particular segment in the traveling direction of the vehicle along the route (Step S42). It selects, for example, a segment on the route from the present location to the destination.

On the other hand, if it is judged in Step S41 that no destination has been specified, the on-road driving strain calculating section 51a judges with reference to the information storage 3 whether driver's driving history related to the map information is available (Step S43). If it is judged that driving history of the driver is available, the on-road driving strain calculating section 51a selects a particular segment in the traveling direction of the vehicle along a route that has been traveled in the past (Step S44). It selects, for example, a segment on the route which has been traveled most frequently in the past.

On the other hand, if it is judged in Step S43 that no driving history of the driver is available, the on-road driving strain calculating section 51a estimates the driving route of the vehicle based on the current location and traveling direction and selects a segment on the route as a particular segment in the traveling direction (Step S45).

Next, the on-road driving strain calculating section 51a obtains road information from the information storage 3, and traffic information (congestion information) via the communications section 4. It calculates the driving strain Ws due to vehicle speed in a sub-segment in the selected particular segment, as described earlier, based on the road information and traffic information (Step S46). Then, the on-road driving strain calculating section 51a calculates the driving strain Wc due to driving operations in the sub-segment in the selected particular segment, as described earlier, based on the road information (Step S47).

Next, the on-road driving strain calculating section 51a obtains weather information via the communications section 4 and calculates the driving strain Ww due to weather in the sub-segment in the selected particular segment, as described earlier, based on the weather information or the like (Step S48). Then, the on-road driving strain calculating section 51a calculates the driving strain Wt due to time of day (hours) in the sub-segment in the selected particular segment, as described earlier, based on the time of passage through the sub-segment (Step S49).

Next, from the driving strains calculated above, the on-road driving strain calculating section 51a calculates the on-road driving strain Wroad by using Equation (1) described earlier(Step S50). Then, the on-road driving strain calculating section 51a judges whether the on-road driving strain Wroad has been calculated for all the sub-segments in the selected particular segment (Step S51). If the on-road driving strain Wroad has not been calculated for all the sub-segments, the on-road driving strain calculating section 51a returns to Step S46, where it calculates the on-road driving strain Wroad for the next sub-segment. When the on-road driving strain Wroad has been calculated for all the sub-segments in the selected particular segment, the on-road driving strain calculating section 51a finishes this process.

The on-road driving strain Wroad calculated by the on-road driving strain calculating section 51a is stored temporarily in the RAM 54.

In the driver condition prediction process (Step S6) of FIG. 7, as shown in FIG. 9, the driver condition predicting section 51b of the CPU 51 obtains the current biomedical information (heart rate, in this case) acquired by the biomedical information acquisition sensor section 1 (Step S61).

Incidentally, the biomedical information acquired periodically (at designated sampling times of the A/D converter) from the biomedical information acquisition sensor section 1 is accumulated in the RAM 54.

Next, the driver condition predicting section 51*b* obtains the on-road driving strains Wroad for all the sub-segments calculated in the on-road driving strain calculation process described above (Step S62).

Next, the driver condition predicting section 51*b* judges whether the vehicle is currently in Pre-start status (including Just Started status) (Step S63). If it is judged that the vehicle is in Pre-start status (including Just Started status), the driver condition predicting section 51*b* goes to a pre-start prediction process (Step S64). On the other hand, if it is judged that the vehicle is not in Pre-start status (including Just Started status), the driver condition predicting section 51*b* goes to a drive-time prediction process (Step S65).

As shown in FIG. 10, in the pre-start prediction process (Step S64), if a driver has been recognized in Step S2 above, the driver condition predicting section 51*b* retrieves unique information to that driver, i.e., the relationship between the heart rate and physiological conditions of the driver as well as relationship between the on-road driving strain Wroad and the driver's heart rate from the database described above (Steps S641 and S642). On the other hand, if a driver has not been recognized, the driver condition predicting section 51*b* retrieves information about general drivers, i.e., the typical relationship between the heart rates and physiological conditions of drivers as well as typical relationship between the on-road driving strain Wroad and heart rates of drivers from the database described above (Steps S641 and S643).

Next, the driver condition predicting section 51*b* converts the on-road driving strain Wroad calculated for consecutive sub-segments in the particular segment into a function of time (Step S644). Then, the driver condition predicting section 51*b* converts the changes in on-road driving strain Wroad expressed as a function of time into changes in heart rate (predicted value)—which is biomedical information—according to certain rules, taking into consideration the heart rate (measured value) acquired by the biomedical information acquisition sensor section 1 (Step S645), as described with reference to FIGS. 3A and 3B. Then, the driver condition predicting section 51*b* predicts the physiological conditions of the driver from the obtained changes in the heart rate of the driver (Step S646) according to the relationship between the heart rate and physiological conditions of the driver retrieved above.

On the other hand, in the drive-time prediction process (Step S65), Step S651 to Step S653 in FIG. 11 are the same as Step S641 to Step S643 in FIG. 10.

In Step S654, the driver condition predicting section 51*b* of the CPU 51 obtains, from the RAM 54, the biomedical information from the start of driving to the present time and the on-road driving strain Wroad from the start of driving to the present time.

As is the case with Step S644 above, the driver condition predicting section 51*b* converts the on-road driving strain Wroad into a function of time (Step S655). Then, the driver condition predicting section 51*b* converts the changes in on-road driving strain Wroad expressed as a function of time into changes in heart rate (predicted value) (Step S656), taking into consideration the heart rate (measured value) acquired by the biomedical information acquisition sensor section 1 and according to certain rules which take into consideration biomedical information at a particular time point during a period from a start of driving to the present time, and the on-road driving strain Wroad from the start of driving to the present time, as described with reference to FIGS. 4A and 4B. In this way, the driver condition predicting section 51*b* predicts the physiological conditions of the driver from the obtained changes in the heart rate of the driver (Step S657) according to the relationship between the heart rate and physiological conditions of the driver, as is the case with Step S646 above.

Returning to FIG. 9, the driver condition predicting section 51*b* determines in Step S66 whether to provide desired information to the driver based on the predicted biomedical information of the driver: for example, whether to give a warning to the driver. If it is determined that the driver should be warned and if, for example, it is predicted that the driver will get sleepy in 40 minutes, the driver condition predicting section 51*b* outputs an audio warning to that effect from the audio output section 6 or displays a warning to that effect in the display section 7 (Step S67). Also, in Step S67, from among the warning lamps 83 on the operation panel 8 shown in FIG. 6, the driver condition predicting section 51*b* changes the color of the lamp 83*e* which corresponds to 40 Minutes Later from yellow to red. Then, the driver condition predicting section 51*b* finishes this process.

Next, in the deviation correction process (Step S8) of FIG. 7, the driver condition predicting section 51*b* of the CPU 51 detects a press of the setting button 84*a* among the deviation correction buttons 84 on the operation panel 8 (Step S81), as shown in FIG. 12. For example, if the driver condition predicting section 51*b* does not predict sleepiness even though the driver feels sleepy, the driver can press the setting button 84*a*. Then, the driver condition predicting section 51*b* detects the press of the button and corrects the deviation between the predicted physiological condition and subjective physiological condition of the driver in the manner described above (so as to increase detection sensitivity to sleepiness, for example) (Step S82).

Also, the driver condition predicting section 51*b* detects a press of the cancel button 84*b* among the deviation correction buttons 84 on the operation panel 8 (Step S83). For example, if the driver condition predicting section 51*b* predicts sleepiness even though the driver does not feel sleepy, the driver can press the cancel button 84*b*. Then, the driver condition predicting section 51*b* detects the press of the button and corrects the deviation between the predicted physiological condition and subjective physiological condition of the driver in the manner described above (so as to decrease detection sensitivity to sleepiness, for example) (Step S84).

If a specific driver has been recognized in Step S2 above, the driver condition predicting section 55*b* reflects the deviation information in the unique information to that driver stored in the database, as described above (Step S85). This makes it possible to gradually improve the prediction accuracy of the physiological conditions of the driver. If a specific driver has not been recognized in Step S2 above, the deviation information is reflected in the information about general drivers.

As described above, according to the first embodiment, since the physiological conditions of the driver on the road to be traveled are predicted more accurately by using biomedical information and on-road driving strain Wroad and the driver is warned in advance of sleepiness and fatigue he/she is likely to experience, he/she can tell effectively when he/she will get sleepy even though he/she is not sleepy at present. Therefore, the driver can take effective measures to avoid danger, such as taking a break in a service area or taking a drink in advance to keep himself/herself awake before getting sleepy while driving on a highway.

Also, since it is judged whether to give a warning, based on the predicted physiological conditions of the driver, and a warning is provided only when it is really needed, any unnecessary warning which will offend the driver can be avoided.

Also, since physiological conditions of the driver are predicted by using driver's unique information, they can be predicted precisely even if there are individual variations, for example, in the relationship between the heart rate and physiological conditions of the driver or between the on-road driving strain Wroad and the driver's heart rate.

Furthermore, since deviations between predicted physiological conditions and subjective physiological conditions of the driver can be corrected easily, any such deviation, when it occurs, can be corrected quickly, resulting in a more precise prediction of the driver's physiological conditions.

Incidentally, in Step S41 of FIG. 8, when the on-road driving strain calculating section 51a judges that a destination has been specified, the on-road driving strain calculating section 51a may search for a plurality of routes to the specified destination, select a particular segment in the traveling direction in each of the routes, and calculate on-road driving strain Wroad by analyzing road information of the particular segment.

In that case, in Step S64 or S65 shown in FIG. 9, the driver condition predicting section 51b will predict the physiological conditions of the driver for the particular segment in each of the routes based on the biomedical information acquired by the biomedical information acquisition sensor section 1, on-road driving strain Wroad calculated by the on-road driving strain calculating section 51a, information stored in the database, etc. (as is the case with the first embodiment described above) and will determine a route which will cause less adverse effect on driving from among the plurality of routes based on the results of the prediction.

For example, from among the plurality of routes, the driver condition predicting section 51b determines a rout which will cause less sleepiness and fatigue or less tension and irritation. Then, the driver condition predicting section 51b provides to the driver the route judged to cause less adverse effect on driving. For example, the driver condition predicting section 51b displays the route which will cause less sleepiness and fatigue on the display screen in the display section 7 to guide the driver. In this way, since a route which will cause less sleepiness and fatigue can be offered to the driver, danger caused by sleepiness and fatigue can be avoided more effectively than according to the above embodiment. This makes a route-finding function in a vehicle navigation system more convenient.

Also, when the driver is driving along the route selected by the on-road driving strain calculating section 51a based on route-finding results, if the driver condition predicting section 51b predicts sleepiness and fatigue on the route due to a change in the situation, the on-road driving strain calculating section 51a may change the route by predicting the physiological conditions of the driver for a particular segment in each of the routes again.

Furthermore, when the driver condition predicting section 51b predicts the physiological conditions of the driver for a particular segment in each of the routes, if it turns out that there is no such route that will not cause, for example, sleepiness, the destination may be changed by the consent of the driver after prompting the driver to change the destination.

(Second Embodiment)

A vehicle navigation system according to a second embodiment is basically analogous to the vehicle navigation system 100 according to the first embodiment in configuration, functionality, and operation, but differs slightly in the technique for predicting the physiological conditions of the driver. Description will be given below mainly of the part which differs from the vehicle navigation system 100 according to the first embodiment.

Whereas in the first embodiment, physiological conditions of the driver are predicted in accordance with the procedures shown in FIG. 10 or 11, in the case of the vehicle navigation system of the second embodiment, physiological conditions of the driver are predicted by using a neural network which has advanced information processing capabilities including learning capabilities.

Figure 13A:
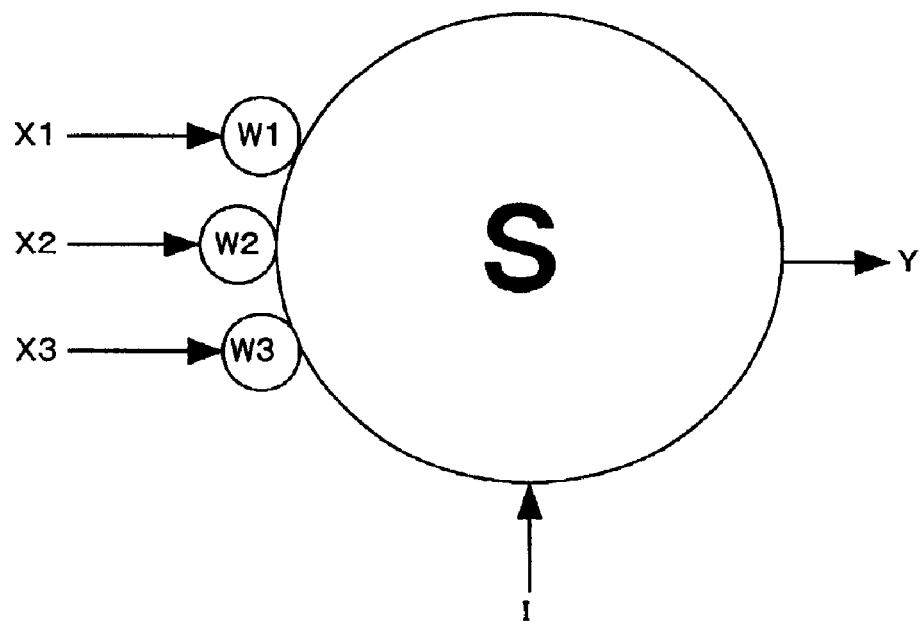
FIG. 13A is a model diagram of a neuron used for a neural network in the driver condition predicting section 51b when performing the process of prediction before start (including prediction just after start) in Step S64 of FIG. 9.
Figure 13B:
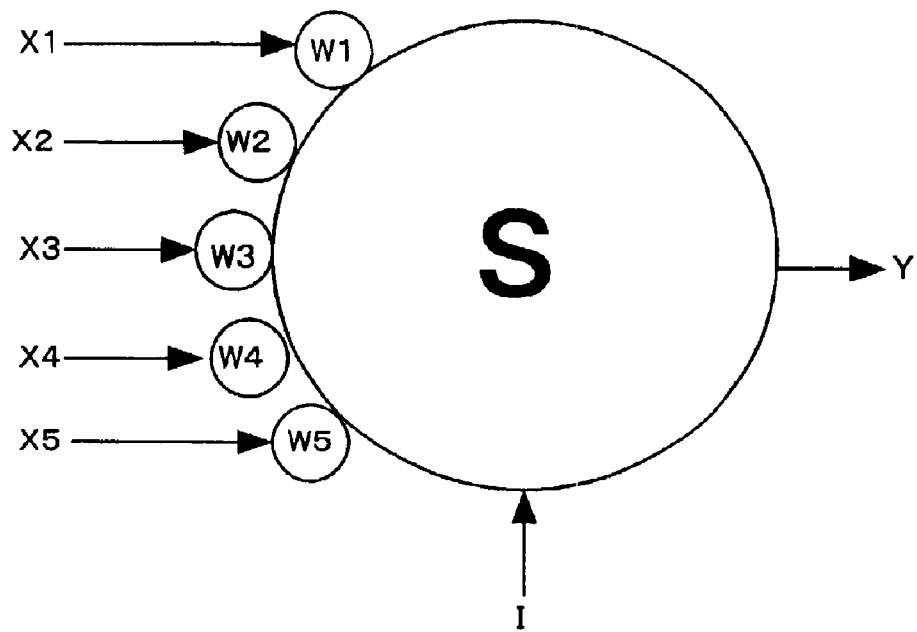
FIG. 13B is a model diagram of a neuron used for the neural network in the driver condition predicting section 51b when performing the drive-time prediction process in Step S65 of FIG. 9.

A neural network has been built logically in the driver condition predicting section 51b according to the second embodiment. FIG. 13A is a model diagram of a neuron used for a neural network in the driver condition predicting section 51b when performing the process of prediction before start (including prediction just after start) in Step S64 of FIG. 9. FIG. 13B is a model diagram of a neuron used for the neural network in the driver condition predicting section 51b when performing the drive-time prediction process in Step S65 of FIG. 9.

In FIG. 13A, reference characters X1 to X3 denote input signals, W1 to W3 denote coupling coefficients (coupling weights), S denotes a neuron state, Y denotes an output signal, and I denotes an instructor signal. For example, the input signal X1 contains the current biomedical information acquired by the biomedical information acquisition sensor section 1, the input signal X2 contains the on-road driving strain Wroad calculated by the on-road driving strain calculating section 51a, and the input signal X3 contains driver-specific information stored in the database. The coupling coefficients W1 to W3 are used to weight the input signals X1 to X3 and are multiplied by X1 to X3, respectively. The coupling coefficients W1 to W3 will change through learning. The neuron state S is calculated, for example, with Equation (2) below (a general formula of a neuron state S).

$$S = W1*X1 + W2*X2 + W3*X3 \qquad (2)$$

The output signal Y is a value (0 to 1) which represents a physiological condition of the driver. It is calculated based on a transfer function which in turn is calculated from the neuron state S. For example, if the output signal Y is equal to or larger than a predicted value of sleepiness d, it is predicted that the driver will get sleepy. The instructor signal I is used for neural network learning. The learning mainly concerns correction of deviation between predicted and subjective physiological conditions of the driver. Details will be described later.

The model diagram in FIG. 13B contains more input signals and coupling coefficients than the model diagram in FIG. 13A. For example,
the input signal X1 contains biomedical information at a particular time point (or in a particular segment) out of the biomedical information acquired by the biomedical information acquisition sensor section 1 during the period from the start of driving to the present time, the input signal X2 contains the current biomedical information acquired by the biomedical information acquisition sensor section 1, the input signal X3 contains the on-road driving strain Wroad calculated by the on-road driving strain calculating section 51a with respect to the road traveled during the period from the start of driving to the present time, the input signal X4 contains the on-road driving strain Wroad calculated by the on-road driving strain calculating section 51a with respect to the road to be traveled, and the input signal X5 contains driver-specific information stored in the database. The neuron state S is calculated, for example, with Equation (3) below (a general formula of a neuron state S).

$$S = W1*X1 + W2*X2 + W3*X3 + W4*X4 + W5*X5 \quad (3)$$

Figure 14:
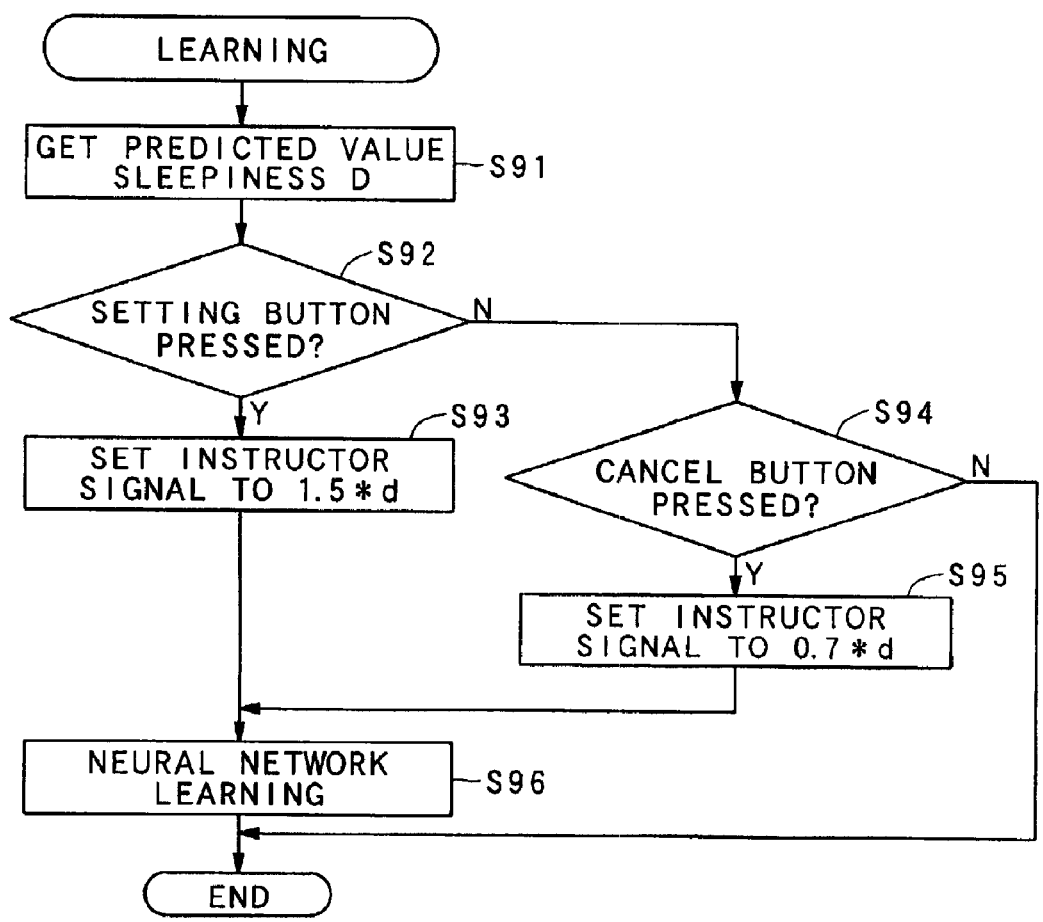
FIG. 14 is a flowchart of processes performed by the driver condition predicting section 51b when the neural network does learning.

FIG. 14 is a flowchart of processes performed by the driver condition predicting section 51b when the neural network does learning. These processes correspond to the deviation correction processes according to the first embodiment shown in FIG. 12.

In FIG. 14, the driver condition predicting section 51b obtains the predicted value of sleepiness d (Step S91). When the setting button 84a among the deviation correction buttons 84 on the operation panel 8 described above is pressed, the driver condition predicting section 51b detects the press (Step S92) and sets the instructor signal I, for example, to 1.5*d (Step S93). This means increasing the detection sensitivity to sleepiness by making the instructor signal I larger than the predicted value of sleepiness d. For example, if the driver condition predicting section 51b does not predict sleepiness even though the driver currently feels sleepy, the driver can press the setting button 84a.

On the other hand, when the cancel button 84b among the deviation correction buttons 84 on the operation panel 8 is pressed, the driver condition predicting section 51b detects the press (Step S94) and sets the instructor signal I, for example, to 0.7*d (Step S95). This means decreasing the detection sensitivity to sleepiness by making the instructor signal I smaller than the predicted value of sleepiness d. For example, if the driver condition predicting section 51b predicts sleepiness even though the driver currently does not feel sleepy, the driver can press the cancel button 84b.

Then, the driver condition predicting section 51b compares the instructor signal I specified in Step S93 or S95 with the output signal Y in the neural network and adjusts the values of the coupling coefficients W1 to W3 in such a way as to minimize error (Step S96). The optimum values of coupling coefficients W1 to W3 are determined through such learning.

As described above, in addition to the benefits of the vehicle navigation system according to the first embodiment described earlier, the second embodiment allows higher-level prediction of the physiological conditions of the driver through the learning capabilities of the neural network.

(Third Embodiment)

Whereas the first and second embodiments use the navigation system installed in the vehicle for the on-road driving strain calculation and driver condition prediction processes described above, a third embodiment uses a stationary server apparatus installed outside the vehicle for on-road driving strain calculation and driver condition prediction processes. Description will be given below mainly of the part which differs from the vehicle navigation system 100 according to the first and second embodiments.

Figure 15:
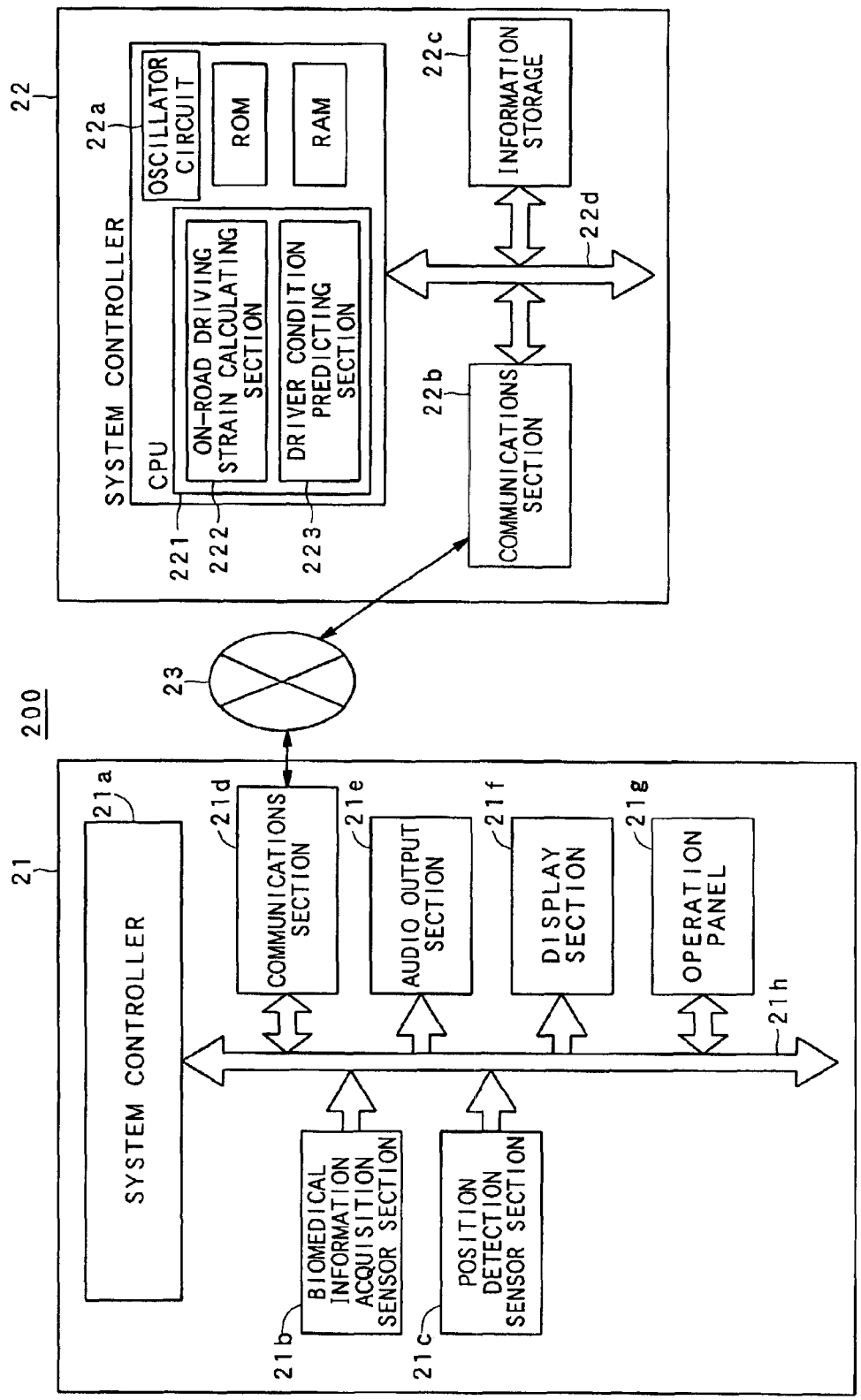
FIG. 15 is diagram showing a simplified exemplary configuration of a vehicle navigation system according to a third embodiment.

FIG. 15 is diagram showing a simplified exemplary configuration of a vehicle navigation system according to the third embodiment. As shown in the figure, a vehicle navigation system 200 includes a stationary server apparatus 22 and a terminal apparatus 21 mounted on a vehicle and capable of communicating with the server apparatus 22 via a mobile communications network 23, which incidentally is a known information and communications network consisting of wireless base stations, leased lines, public lines, etc.

The terminal apparatus 21 includes a system controller 21a, biomedical information acquisition sensor section 21b, position detection sensor section 21c, communications section 21d, audio output section 21e, display section 21f, and operation panel 21g, which are mutually connected via a bus 21h.

The system controller 21a has a CPU which functions as information providing device, an oscillator circuit, a ROM which stores programs and data for controlling various operations, and a RAM which serves as a working area. It controls the operation of the entire terminal apparatus 21.

The biomedical information acquisition sensor section 21b corresponds to the biomedical information acquisition sensor section 1 of the first embodiment and functions as biomedical information acquisition device for acquiring biomedical information of the driver. Also, the position detection sensor section 21c, communications section 21d, audio output section 21e, display section 21f, and operation panel 21g serve the same functions as the position detection sensor section 1, communications section 4, audio output section 6, display section 7, and operation panel 8, respectively, according to the first embodiment.

Also, the communications section 21d functions as transmitting device for transmitting the biomedical information acquired by the biomedical information acquisition sensor section 21b to the server apparatus 22 via the mobile communications network 23 and as receiving device for receiving various information about predicted physiological conditions of the driver from the server apparatus 22 via the mobile communications network 23.

When the driver presses a button on the operation panel 21g, an appropriate detection signal is sent to the server apparatus 22 via the communications section 21d and mobile communications network 23.

The server apparatus 22 includes a system controller 22a, communications section 22b, and information storage 22c, which are mutually connected via a bus 22d.

The system controller 22a has a CPU 221 which performs computational functions, an oscillator circuit, a ROM which stores programs and data for controlling various operations, a RAM which serves as a working area, etc. It controls the operation of the entire server apparatus 22 and comprises clock functions. The information providing programs stored in the ROM make the CPU 221 function as an on-road driving strain calculating section 222 and a driver condition predicting section 223. The on-road driving strain calculating section 222 and driver condition predicting section 223 serve the same functions, respectively, as the on-road driving strain calculating section 51a and driver condition predicting section 51b according to the first or second embodiment and perform the processes of the first embodiment shown in FIG. 7.

The communications section 22b functions as receiving device for receiving biomedical information from the terminal apparatus 21 and as transmitting device for transmitting various information about the predicted physiological conditions of the driver to the terminal apparatus 21 via the mobile communications network 23.

The information storage 22c serves the same functions as the information storage 3 of the first embodiment.

With this configuration, on the terminal apparatus 21, biomedical information (e.g., heart rate) of the driver is acquired by the biomedical information acquisition sensor section 21b and transmitted by the communications section 21d to the server apparatus 22 via the mobile communications network 23. On the server apparatus 22, the biomedical information transmitted from the terminal apparatus 21 is received by the communications section 22b and on-road driving strain Wroad is calculated by the on-road driving strain calculating section 222 by analyzing road information of a particular segment in the traveling direction of the vehicle.

For example, as the driver specifies a destination using the operation panel 21g of the terminal apparatus 21, this information is transmitted to the server apparatus 22 via the communications section 21*d* and the mobile communications network 23. On the server apparatus 22, the destination information transmitted from the terminal apparatus 21 is received by the communications section 22*b*. Then the on-road driving strain calculating section 222 of the server apparatus 22 selects a particular segment in the traveling direction of the vehicle based on a route to the specified destination, analyzes road information of that segment, and calculates on-road driving strain Wroad.

The server apparatus 22 predicts the physiological conditions of the driver in the particular segment in the traveling direction of the vehicle using the biomedical information received by the driver condition predicting section 223 and the calculated on-road driving strain Wroad. Based on the physiological conditions of the driver thus predicted, the driver condition predicting section 223 of the server apparatus 22 determines whether to provide desired information to the driver. If it is determined that desired information should be provided, the driver condition predicting section 223 transmits information to the effect, for example, that the driver will get sleepy in a few tens of minutes to the terminal apparatus 21 via the communications section 22*b* and mobile communications network 23. On the terminal apparatus 21, the information transmitted from the server apparatus 22 is received by the communications section 22*b*, a warning, for example, that the driver will get sleepy in a few tens of minutes is output by the system controller 21*a* from the audio output section 21*e* and display section 21*f*, and an appropriate lamp among the warning lamps on the operation panel 21*g* glows red.

As described above, the third embodiment offers the same effect as the vehicle navigation system of the first and second embodiments by using communications functions even if the on-road driving strain calculating section and driver condition predicting section are installed outside the vehicle.

Incidentally, although according to the above embodiments, a warning that the driver will get sleepy in a few tens of minutes has been cited as an example of the desired information provided by the driver condition predicting section 51*b* or 223 after prediction of the physiological conditions of the driver, the present invention is not limited to this. For example, it may be configured such that a few minutes before the driver gets sleepy, the driver condition predicting section 51*b* or 223 will select a piece of music which will shake off sleepiness, read it from the information storage 3 or 22*c*, and play it back through the audio output section 6 or 21*e*.

Besides, according to the above embodiments, sleepiness is predicted and the driver is warned of it, but the present invention may also be configured to predict irritation and warn the driver of it. This can prevent any accident caused by overspeed as a result of irritation.

Besides, according to the above embodiments, physiological conditions such as sleepiness, fatigue, concentration, tension, and irritation are predicted based on heart rate taken as an example of biomedical information, but the present invention is not limited to this. It can provide the same benefits as the above embodiments if configured to predict physiological conditions based, for example, on respiration, fluctuations in heartbeat, nictitation, and complexion acquired by the biomedical information acquisition sensor section 1.

Besides, according to the above embodiments, physiological conditions include sleepiness, fatigue, concentration, tension, and irritation, but the present invention is not limited to them. It may include, for example, nausea and dizziness. The present invention can provide more accurate predictions if configured to predict nausea and dizziness using, for example, such biomedical information as complexion changes and on-road driving strain Wroad.

Besides, according to the above embodiments, physiological conditions of the driver are predicted based on biomedical information, but the present invention may also be configured to predict physiological conditions of the driver based on the sound volume or content of the music or radio which the driver listens to. Although the purpose of listening to the car radio varies from person to person, physiological conditions of the driver can be predicted by checking the sound volume, etc. of music or radio if he/she calms himself/herself by listening to soothing music when irritated or listens to vigorous music with the volume turned up when he/she feels sleepy.

Besides, according to the above embodiments, the information providing system according to the present invention is applied to a vehicle navigation system, but the present invention is not limited to this. For example, it may also be applied to traffic control systems. In that case, the present invention can predict physiological conditions of the driver and inform a traffic controller about it, making it possible to change a route and give instructions according to the physiological conditions of the driver. Also, the traffic controller can ask drivers about physiological conditions and store the answers in the database as unique information to the respective drivers.

As described above, since the present invention is configured to predict physiological conditions of the driver using biomedical information of the driver and on-road driving strain of a road, it can predict physiological conditions of the driver on the road ahead more accurately. Thus, it can make the driver avoid danger reliably by making him/her aware of the predicted physiological conditions.

Also, since physiological conditions of the driver are predicted using driver-specific information, they can be predicted precisely even if there are individual variations, for example, in the relationship between the heart rate and physiological conditions of the driver or between the on-road driving strain and the driver's heart rate.

Furthermore, since deviations between predicted physiological conditions and subjective physiological conditions of the driver can be corrected, any such deviation, when it occurs, can be corrected quickly, resulting in a more precise prediction of the driver's physiological condition.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

The entire disclosure of Japanese Patent Application No. 2001-257434 filed on Aug. 28, 2001 including the specification, claims, drawings and summary is incorporated herein by reference in its entirety.

What is claimed is:

1. An information providing system which provides desired information to a driver who drives a vehicle, comprising:

a biomedical information acquisition device which acquires biomedical information of the driver;

an on-road driving strain calculating device which calculates on-road driving strain effecting the driver's operating load by analyzing road information of a particular segment in a traveling direction of the vehicle; and a driver condition predicting device which predicts physiological condition of the driver in the particular segment by using the acquired biomedical information and the calculated on-road driving strain.

2. The information providing system according to claim 1, wherein the driver condition predicting device further judges whether to provide the desired information to the driver based on the predicted physiological condition of the driver.

3. The information providing system according to claim 1, wherein before or just after the vehicle starts, the driver condition predicting device predicts the physiological condition of the driver in the particular segment by using the acquired biomedical information at the present time and the calculated on-road driving strain with respect to the road to be traveled.

4. The information providing system according to claim 1, wherein when the vehicle is running, the driver condition predicting device predicts the physiological condition of the driver in the particular segment by using the acquired biomedical information at a particular time point during a period from a start of driving to the present time, the acquired biomedical information at the present time, and calculated on-road driving strain with respect to the road to be traveled.

5. The information providing system according to claim 1, wherein the driver condition predicting device predicts the physiological condition of the driver in the particular segment further by using the driver's unique information stored in a database.

6. The information providing system according to claim 5, wherein the driver condition predicting device stores a relationship between the acquired biomedical information and the calculated on-road driving strain in a database as the driver's unique information.

7. The information providing system according to claim 1, further comprising a correction signal input device which inputs a correction signal for correcting deviation between the predicted driver's physiological condition and subjective physiological condition of the driver, wherein when the correction signal is input, the driver condition predicting device corrects the deviation between the predicted physiological condition of the driver and the subjective physiological condition of the driver.

8. The information providing system according to claim 7, wherein when the deviation is corrected, the driver condition predicting device reflects the deviation information in the driver's unique information stored in the database.

9. The information providing system according to claim 1, further comprising a navigation guidance device which guides the vehicle along its route, wherein the on-road driving strain calculating device selects the particular segment in the traveling direction by using map information obtained from the navigation guidance device.

10. The information providing system according to claim 9, wherein the on-road driving strain calculating device selects the particular segment in the traveling direction based on the driver's driving history related to the map information.

11. The information providing system according to claim 9, wherein the on-road driving strain calculating device searches for a route to a destination specified by the driver and selects the particular segment in the traveling direction based on the search result.

12. The information providing system according to claim 11, wherein:

the on-road driving strain calculating device searches for a plurality of routes to the destination specified by the driver, selects the particular segment in the traveling direction in each of the routes, and calculates on-road driving strain by analyzing road information of the particular segment; and the driver condition predicting device predicts the physiological condition of the driver in the particular segment in each of the routes by using the acquired biomedical information and the calculated on-road driving strain and determines a route which will cause less adverse effect on driving from among the plurality of routes based on the result of the prediction.

13. The information providing system according to claim 12, wherein the driver condition predicting device provides to the driver the determined route which will cause less adverse effect on driving.

14. The information providing system according to claim 1, wherein the on-road driving strain calculating device calculates on-road driving strain by analyzing the road information in consideration of weather in the particular segment.

15. The information providing system according to claim 1, wherein the on-road driving strain calculating device calculates on-road driving strain by analyzing the road information in consideration of time in the particular segment.

16. The information providing system according to claim 1, wherein the biomedical information includes heart rate, respiration, fluctuations in heartbeat, nictitation, and complexion.

17. An information providing method which provides desired information to a driver who drives a vehicle, comprising:

a step of acquiring biomedical information of the driver;

a step of calculating on-road driving strain effecting the driver's operating load by analyzing road information of a particular segment in a traveling direction of the vehicle; and a driver condition predicting step of predicting physiological condition of the driver in the particular segment by using the acquired biomedical information and the calculated on-road driving strain.

18. The information providing method according to claim 17, wherein the driver condition predicting step further includes judging whether to provide the desired information to the driver based on the predicted physiological condition of the driver.

19. An information providing method which provides desired information to a driver who drives a vehicle, comprising the steps of:

acquiring biomedical information of the driver;

searching for a plurality of routes to a destination specified by the driver and calculating on-road driving strain in each of the routes by analyzing road information of a particular segment in a traveling direction of the vehicle; and predicting physiological condition of the driver in the particular segment in each of the routes by using the acquired biomedical information and the calculated on-road driving strain and determining a route which will cause less adverse effect on driving from among the plurality of routes based on the result of the prediction.

20. An information recorded medium wherein an information providing program for providing desired information to a driver who drives a vehicle, is recorded so as to be read by a computer, the program makes the computer function as:

a biomedical information acquisition device which acquires biomedical information of the driver;

an on-road driving strain calculating device which calculates on-road driving strain effecting the driver's operating load by analyzing road information of a particular segment in a traveling direction of the vehicle; and a driver condition predicting device which predicts physiological condition of the driver in the particular segment by using the acquired biomedical information and the calculated on-road driving strain.

21. The information providing program according to claim 20, wherein the driver condition predicting device further judges whether to provide the desired information to the driver based on the predicted physiological condition of the driver.

22. The information providing program according to claim 20, wherein the driver condition predicting device predicts the physiological condition of the driver in the particular segment further by using the driver's unique information stored in a database.

23. The information providing program according to claim 20, wherein when a correction signal for correcting the deviation between the driver's physiological conditions predicted by the driver condition predicting device and subjective physiological conditions of the driver is input, the driver condition predicting device corrects the deviation between the predicted physiological condition of the driver and the subjective physiological condition of the driver.

24. An information recorded medium wherein an information providing program for providing desired information to a driver who drives a vehicle, is recorded so as to be read by a computer, the program makes the computer function as:

a biomedical information acquisition device which acquires biomedical information of the driver;

an on-road driving strain calculating device which searches for a plurality of routes to a destination specified by the driver and calculates on-road driving strain in each of the routes by analyzing road information of a particular segment in a traveling direction of the vehicle; and a driver condition predicting device which predicts the physiological conditions of the driver in the particular segment in each of the routes by using the acquired biomedical information and the calculated on-road driving strain and determines a route which will cause less adverse effect on driving from among the plurality of routes based on the results of the prediction.

25. An information providing system which has a server apparatus installed at a fixed location and a terminal apparatus mounted on a vehicle and capable of communicating with the server apparatus via a mobile communications network and which provides desired information to a driver who drives the vehicle, wherein the terminal apparatus comprises:

a biomedical information acquisition device which acquires biomedical information of the driver; and a transmitting device which transmits the acquired biomedical information to the server apparatus via the mobile communications network, and the server apparatus comprises:

a receiving device which receives the biomedical information transmitted from the terminal apparatus;

an on-road driving strain calculating device which calculates on-road driving strain effecting the driver's operating load by analyzing road information of a particular segment in the traveling direction of the vehicle; and a driver condition predicting device which predicts physiological condition of the driver in the particular segment by using the received biomedical information and the calculated on-road driving strain.

26. A server apparatus comprising:

a receiving device which receives biomedical information of a driver transmitted from a terminal apparatus mounted on a vehicle via a mobile communications network;

an on-road driving strain calculating device which calculates on-road driving strain effecting the driver's operating load by analyzing road information of a particular segment in a traveling direction of the vehicle; and a driver condition predicting device which predicts physiological condition of the driver in the particular segment by using the received biomedical information and the calculated on-road driving strain.

27. A terminal apparatus mounted on a vehicle, comprising:

a biomedical information acquisition device which acquires biomedical information of a driver;

a transmitting device which transmits the acquired biomedical information to a server apparatus via a mobile communications network;

a receiving device which receives information about predicted physiological condition of the driver transmitted from the server apparatus via the mobile communications network; the predicted physiological condition being predicted by using the biomedical information and on-road driving strain effecting the driver's operating load in the server apparatus; and an information providing device which provides the desired information to the driver based on the received information about the physiological condition.

28. An information providing system which provides desired information to a driver who drives a vehicle, comprising:

a biomedical information acquisition device which acquires biomedical information of the driver;

an on-road driving strain calculating device which searches for a plurality of routes to a destination specified by the driver and calculates on-road driving strain in each of the routes by analyzing road information of a particular segment in a traveling direction of the vehicle; and a driver condition predicting device which predicts the physiological conditions of the driver in the particular segment in each of the routes by using the acquired biomedical information and the calculated on-road driving strain and determines a route which will cause less adverse effect on driving from among the plurality of routes based on the results of the prediction.

* * * * *